(12) United States Patent
Heim et al.

(10) Patent No.: US 11,534,228 B2
(45) Date of Patent: *Dec. 27, 2022

(54) ILLUMINATED ELECTROSURGICAL SYSTEM AND METHOD OF USE

(71) Applicant: Invuity, Inc., San Francisco, CA (US)

(72) Inventors: Warren P. Heim, Boulder, CO (US);
Alex Vayser, Mission Viejo, CA (US);
David Wayne, Watsonville, CA (US);
Jason Hegener, San Francisco, CA (US)

(73) Assignee: Invuity, Inc., San Francisco, CA (US)

( * ) Notice: Subject to any disclaimer, the term of this patent is extended or adjusted under 35 U.S.C. 154(b) by 314 days.

This patent is subject to a terminal disclaimer.

(21) Appl. No.: 16/686,749

(22) Filed: Nov. 18, 2019

(65) Prior Publication Data

US 2020/0085489 A1 Mar. 19, 2020

Related U.S. Application Data

(63) Continuation of application No. 14/817,966, filed on Aug. 4, 2015, now Pat. No. 10,499,974.

(Continued)

(51) Int. Cl.
*A61B 18/18* (2006.01)
*A61B 18/12* (2006.01)
(Continued)

(52) U.S. Cl.
CPC ...... *A61B 18/1206* (2013.01); *A61B 18/1402* (2013.01); *A61B 90/30* (2016.02);
(Continued)

(58) Field of Classification Search
CPC ............ A61B 18/1206; A61B 18/1402; A61B 19/5202; A61B 2018/00178;
(Continued)

(56) References Cited

U.S. PATENT DOCUMENTS 3,677,262 A 7/1972 Zukowski
4,562,838 A 1/1986 Walker
(Continued)

FOREIGN PATENT DOCUMENTS

DE 102008019313 10/2009
EP 1440665 B1 5/2005
(Continued)

OTHER PUBLICATIONS

European search report with written opinion dated Mar. 1, 2018 for EP Application No. 15831605.
(Continued)

*Primary Examiner* — Michael F Peffley
*Assistant Examiner* — Amanda L Zink
(74) *Attorney, Agent, or Firm* — McDonnell Boehnen Hulbert & Berghoff LLP

(57) ABSTRACT

A surgical system that illuminates a surgical site using one or more illumination means is powered by radiofrequency energy produced by an electrosurgical generator. Illumination may occur whether or not current is being delivered from an active electrode to target tissue.

20 Claims, 20 Drawing Sheets

Related U.S. Application Data

(60) Provisional application No. 62/036,547, filed on Aug. 12, 2014.

(51) Int. Cl.
*A61B 18/14* (2006.01)
*A61B 90/30* (2016.01)
*A61B 18/00* (2006.01)
*A61B 90/00* (2016.01)

(52) U.S. Cl.
CPC .............. *A61B 90/361* (2016.02); *A61B 2018/00178* (2013.01); *A61B 2018/00589* (2013.01); *A61B 2018/00601* (2013.01); *A61B 2018/1266* (2013.01); *A61B 2090/308* (2016.02)

(58) Field of Classification Search
CPC .......... A61B 2018/00589; A61B 2018/00601; A61B 2018/1266; A61B 2019/5208; A61B 90/30
See application file for complete search history.

(56) References Cited

U.S. PATENT DOCUMENTS

| | | | |
|---|---|---|---|
| 4,597,030 A | 6/1986 | Brody et al. | |
| 4,688,569 A | 8/1987 | Rabinowitz | |
| 4,856,514 A | 8/1989 | Rabinowitz | |
| 5,613,966 A * | 3/1997 | Makower | A61B 18/1206 604/30 |
| 5,817,091 A | 10/1998 | Nardella et al. | |
| 6,068,627 A * | 5/2000 | Orszulak | A61B 18/12 606/34 |
| 6,504,985 B2 | 1/2003 | Parker et al. | |
| 6,528,954 B1 | 3/2003 | Lys et al. | |
| 6,550,926 B2 | 4/2003 | Berger | |
| 7,083,601 B1 | 8/2006 | Cosmescu | |
| 8,287,534 B2 | 10/2012 | Balog | |
| 8,506,565 B2 | 8/2013 | DeCarlo | |
| 8,690,872 B2 | 4/2014 | Jayaraj | |
| 8,784,416 B2 | 7/2014 | Balog | |
| 8,882,767 B2 | 11/2014 | Greep et al. | |
| 8,882,768 B2 | 11/2014 | Greep et al. | |
| 9,237,922 B2 | 1/2016 | Bromley et al. | |
| 9,259,260 B2 | 2/2016 | Greep et al. | |
| 9,289,212 B2 | 3/2016 | Shelton et al. | |
| 9,289,261 B2 | 3/2016 | Shvetsov et al. | |
| 9,375,253 B2 | 6/2016 | Greep et al. | |
| D761,962 S | 7/2016 | Fleenor | |
| 10,188,393 B2 | 1/2019 | Smith et al. | |
| 10,499,974 B2 | 12/2019 | Heim et al. | |
| 10,813,628 B2 | 10/2020 | Gregg | |
| 2002/0058938 A1 | 5/2002 | Cosmescu | |
| 2002/0107517 A1 * | 8/2002 | Witt | A61B 18/1442 606/50 |
| 2002/0111624 A1 | 8/2002 | Witt et al. | |
| 2004/0030328 A1 | 2/2004 | Eggers et al. | |
| 2004/0162552 A1 | 8/2004 | McClurken | |
| 2005/0171408 A1 * | 8/2005 | Parker | A61B 90/36 600/249 |
| 2006/0282072 A1 | 12/2006 | DesRosier | |
| 2007/0049927 A1 | 3/2007 | Saltzman | |
| 2007/0259308 A1 * | 11/2007 | Rogovsky | A61C 1/00 433/29 |
| 2008/0147058 A1 * | 6/2008 | Horrell | A61B 90/30 606/37 |
| 2009/0054890 A1 | 2/2009 | DeCarlo | |
| 2009/0209979 A1 | 8/2009 | Yates et al. | |
| 2010/0145333 A1 | 6/2010 | Dethier et al. | |
| 2011/0060332 A1 | 3/2011 | Cheng | |
| 2011/0190768 A1 | 8/2011 | Shvetsov et al. | |
| 2012/0265278 A1 | 10/2012 | Fourkas et al. | |
| 2012/0283718 A1 | 11/2012 | Cosmescu | |
| 2012/0283728 A1 | 11/2012 | Cosmescu | |
| 2014/0276763 A1 | 9/2014 | Greep et al. | |
| 2014/0293590 A1 | 10/2014 | Pathy | |
| 2015/0157390 A1 | 6/2015 | Fleenor | |
| 2016/0262825 A1 | 9/2016 | Jayaraj | |
| 2016/0278874 A1 | 9/2016 | Fleenor | |

FOREIGN PATENT DOCUMENTS

| | | |
|---|---|---|
| EP | 1330991 B1 | 9/2007 |
| EP | 3040041 A3 | 11/2016 |
| JP | S59-071743 | 4/1984 |
| JP | H05-184589 | 7/1993 |
| JP | H10-028152 | 1/1998 |
| JP | 11-226026 | 8/1999 |
| JP | 3120330 U | 3/2006 |
| JP | 2009-151949 | 7/2009 |
| KR | 101027819 | 4/2011 |
| WO | 2010016139 | 2/2010 |
| WO | 2010016259 | 1/2012 |
| WO | 2012118746 A2 | 9/2012 |
| WO | 2014036118 A1 | 3/2014 |
| WO | 2014165551 A1 | 10/2014 |
| WO | 2015085108 A1 | 6/2015 |
| WO | 2016196562 A1 | 12/2016 |

OTHER PUBLICATIONS

International search report and written opinion dated Jan. 7, 2016 for PCT Application No. PCT/US15/43677.

* cited by examiner

ILLUMINATED ELECTROSURGICAL SYSTEM AND METHOD OF USE

CROSS-REFERENCE

The present application is a continuation of U.S. patent application Ser. No. 14/817,966, filed Aug. 4, 2015 (now issued as U.S. Pat. No. 10,499,974), which is a non-provisional of, and claims the benefit of U.S. Provisional Patent Application No. 62/036,547 filed Aug. 12, 2014; the entire contents of which are incorporated herein by reference.

BACKGROUND OF THE INVENTION

1. Field of the Invention. The present application generally relates to medical devices, systems and methods, and more particularly relates to illuminated electrosurgical devices and systems and methods of use.

Illumination of a surgical site whether in an open surgical procedure or a minimally invasive surgical procedure, is important since it allows a surgeon to clearly observe the surgical site. Currently available surgical site illumination takes on many forms including overhead lighting, head lamps, illumination elements mounted on surgical instruments, etc. While these commercially available devices can facilitate illumination of a surgical site, in certain circumstances, they may not be optimal. For example, many illumination devices utilize fiber optic cables to deliver light from a light source to the surgical site. These cables as well as other cables and tubing (e.g. electrosurgical instrument cables, suction tubing, etc.) can become entangled thereby inconveniencing the surgeon. Many of these systems do not deliver light to the surgical site efficiently, thus the surgical site may not be adequately illuminated because light is lost as it travels from the light source toward the surgical site. Light loss can also lead to excessive heating of the illumination element or surgical instrument and this can result in patient burns or overheating and damage to the illumination device or surgical instrument. Head lamps can be heavy and awkward to use and require the surgeon to constantly turn his or her head to direct the illumination. Overhead lights require constant adjustment and can cast shadows in the surgical site. Therefore, it would be desirable to provide illuminated surgical instruments that provide lighting closer to the surgical site. Such devices are preferably low profile in order to avoid obstructing the surgical site, and have better cable management features thus improved ergonomics and minimal thermal spread.

Often during surgery, an electrosurgical instrument is used to facilitate tissue cutting or coagulation. Some of these electrosurgical instruments include illumination elements for providing light to the surgical site during electrosurgery. However, the illumination element either requires its own, separate power source often located in the handpiece or a separate housing off the field. In other commercially available devices, power may be obtained from the electrosurgical power unit, however only while the electrosurgical instrument is delivering current to tissue and in contact with tissue in the surgical site. Thus, additional illumination must be provided when the electrosurgical instrument is not delivering current to the tissue and not in contact with the tissue. Therefore, it would be desirable to provide an electrosurgical instrument than can illuminate the surgical site when the electrosurgical instrument is not delivering current to the tissue and that does not necessarily need an additional power source other than the electrosurgical generator, or that is powered indirectly by the generator (e.g. a battery). This permits the surgical site to be illuminated whether or not electrosurgery is being performed. The illumination element may be disposed on the electrosurgical instrument, and it would be desirable if the illumination element has a low profile in order not to obstruct access to the surgical site. Also, it would be desirable if the illumination element does not add excessive weight to the surgical instrument, and can easily be actuated during a surgical procedure. At least some of the objectives will be satisfied by the exemplary embodiments disclosed herein.

2. Description of the Background Art. Patents and publications which are related to illuminated surgical instruments include but are not limited to: U.S. Pat. Nos. 8,506,565; 8,287,534; 6,528,954; 6,504,985; and 4,597,030. Related patent publications also include US Patent Publication Nos. 20070049927; and 20120283718.

SUMMARY OF THE INVENTION

The present application generally relates to medical systems, devices and methods, and more particularly relates to illuminated surgical devices, systems and methods, including but not limited to illuminated electrosurgical instruments, systems, and methods of use. Other surgical devices requiring power such as cameras or sensors may also be powered using the techniques described herein. Additionally, other methods requiring power for feedback devices such as alpha numeric displays, indicator LEDs, etc. may obtain power using the techniques disclosed herein.

Some embodiments provide a surgical site illumination method and assembly which employ electrical energy using a primary source outside of the surgical handpiece that may be used with a general purpose electrosurgical generator using monopolar or bipolar connections typically employed on such generators.

The method may comprise the steps of using surgical instruments that contain one or more elements of predetermined type to influence the manner in which energy transfers and thereby alter how energy is applied to one or more illumination sources to illuminate tissue. Some embodiments can be used to effectively extract energy from the RF power supplied by electrosurgical generators to provide illumination whether or not RF power is simultaneously applied to the tissue during electrosurgery.

The high voltage RF power from the generator may be converted to energy used to power an illumination element (sometimes also referred to herein as illumination power), or energy used to power other surgical equipment, and that is compatible with surgical site illumination sources of the type deployable in a surgical instrument handpiece, such as power that has suitably low voltage, while simultaneously providing the high voltage RF power needed for the surgical procedure. The illumination power conversion may employ dissipative voltage reduction components such as one or more resistive voltage dividers. The illumination power conversion may employ non-dissipative voltage reduction components such as one or more reactive voltage dividers which may have two or more capacitive elements. The illumination power conversion may employ non-dissipative voltage reduction components such as inductors configured as transformers. The illumination power conversion may employ components that adapt the voltage reduction in response to the RF input power conditions such as input voltage, frequency, or waveform. The response to RF input conditions may employ components that alter the configuration or deployment of one or more voltage dividers by switching between two or more current paths. The illumination power conversion may employ one or more components that preferentially pass current of one polarity compared to another polarity, such as diodes.

Reducing energy losses benefits operation by keeping components from heating and by allowing more of the energy supplied by the generator to be applied to the tissue. To reduce energy losses the illumination power conversion may employ multiple electric current pathways selected, such as by using mechanical or electronic switching means or a combination of such means, based on one or more electrical parameters such as frequency, voltage, or current. For example, one or more electronic switching means responsive to the voltage after voltage reduction may be used to select an electric current path that leads to the reduced voltage falling within a predetermined voltage range. The alternative electric current paths may be dissipative or non-dissipative with non-dissipative paths facilitating efficient energy use. Employing switching means responsive to one or more electrical parameter such as frequency and voltage facilitates adapting to the various output power conditions from generators. Non-dissipative voltage divider elements may perform differently based upon the electrical power entering them, such as frequency, and employing one or more switching means responsive to the reduced voltage facilitates efficient voltage reduction. Rather than switches responsive to one or more electrical parameters after the voltage is reduced the switches in one alternative embodiment may respond to one or more input electrical parameters such as frequency, voltage, or current.

In some embodiments, at least a portion of the radiofrequency electrical power from the generator is rectified to direct current. Rectification may be done before voltage reduction, although rectification after voltage reduction allows using rectifying components that operate at lower voltages which can have advantages such as using components that operate more efficiently or have lower cost. Rectification means may include one or more electronic components such as one or more diodes and/or one or more capacitors. The rectification means may include using partial wave rectification, such as a half wave rectifier, or full-wave rectification may be used with a bridge rectifier, for example. Another aspect may involve using one or more components, such as one or more inductors or transformers, in conjunction with rectification means to accomplish at least some voltage reduction and at least some rectification together. Such a combination of a transformer and a rectifier could form a full-wave rectifier.

Optionally, any embodiment may include means to supply electrical power to one or more illumination means (also referred to herein as an illumination element), or any other surgical device requiring power such as a camera, sensor, etc. Illumination means may operate from alternating current, such as reduced voltage radiofrequency power, or from direct current, such as after rectification means has been applied to radiofrequency power. Illumination means may include, for example, one or more incandescent lamps or one or more light emitting diodes (LEDs). LEDs may be any LED known in the art, such as OLEDs, RGB LEDs, etc. Laser diodes may be instead of an LED. Illumination means may also be devices employing gas discharge such as neon lamps.

Other embodiments may include means to control current or voltage provided to one or more illumination means. Such control means may deliver voltage or current within a predetermined range and control the output voltage or current to be within the predetermined range independent of the input electrical power characteristics such as voltage, current, or frequency.

Other embodiments may include means that allow illumination when electrosurgical generator power is not supplying power. Such alternate power means may include a power source in the handpiece or in a connector module that connects to an electrosurgical generator or that is in line between a connector that connects to an electrosurgical generator and a handpiece. The alternate power source may include chemically produced electrical power sources such as batteries or fuel cells or power sources that store energy taken from the electrosurgical generator when it is supplying power to tissue such as using chemical means in a rechargeable battery or using electrical fields or polarized materials such as in one or more capacitors.

Other embodiments may provide switch control means activated by one or more users that activate the generator leading to power being available for providing power for illumination while simultaneously applying power to tissue. Providing switch control means activated by one or more users may activate the generator leading to power being available for illumination without simultaneously providing power for application to tissue. Providing switch control means activated by one or more users may activate the generator leading to power being available for application to tissue without simultaneously providing power for illumination. In other embodiments providing switch control means activated by one or more users does not activate the generator to provide power to tissue and such switch activation provides power for illumination from a power source other than the generator such as from a chemically produced power source. This power source may include a battery or fuel cell or an energy storage means using fields or polarized materials such as capacitors. Such power source may be located, in the handpiece, in a connector module that connects to the generator, or in an inline pendant module between a connector and the handpiece, or between one or more connectors. Other locations are also possible.

The power plug may connect to a wire this is electrically coupled to an electrosurgical accessory. The proximal end of the part of the electrosurgical accessory held by a surgeon usually has a handpiece (also referred to as a handle) into which this wire passes. From there it connects, either directly or indirectly via intermediate electrical conductors, to an active electrode. The active electrode may be in the distal tip of the accessory handpiece. Active electrodes may take on many forms such as blades, hooks, balls, spatulas, loops, tubes with fluid passages, and members of forceps, graspers, and scissors. Active electrodes may be one element of bipolar devices or they may be part of a monopolar configuration. Active electrodes may be used for cutting, coagulation, desiccation, fulguration, ablation, tissue shrinkage, or other purposes for which electrosurgery is used in either monopolar or bipolar applications.

A continuous RF electrical energy path may exist from the electrosurgical generator to the active electrode when energy is applied to the surgical site. The metallic connector for the return line in the return plug may connect to a wire in the return plug and this wire may exit the distal end of the return plug and continues to the proximal end of an electrosurgical accessory handpiece for bipolar devices or to a separate return path device when used for monopolar applications. In the case of bipolar devices, the proximal end of the electro surgical accessory may have a handle into which the return wire passes. From there it may connect directly or indirectly via intermediate electrical conductors, to one or more return path devices such as return electrodes. Return electrodes in bipolar applications have one or more metallic or other electrically conductive elements that directly or indirectly contact patient tissues. Return electrodes provide an energy return path by providing an electrically conductive return path to a lower potential state, e.g. ground in the electrosurgical power supply thereby allowing current supplied by the generator and delivered to the tissue to complete the electrical circuit by returning to the power supply.

Direct contact with patient tissues occurs when the active electrode or return path element contacts patient tissues. Indirect contact with patient tissue occurs when an intermediate substance, such as conductive liquids, including solutions that contain blood or saline or other electrolytes, conducts electrical energy for at least part of the energy flow path.

Electronic circuits, including those for the voltage reduction means, rectification means, and electrical control means, may be designed to reduce sensitivity to generator frequency and other variables by including passive components such as inductors, resistors, and capacitors and/or active components such as diodes (including silicon diodes, Schottky diodes, zener diodes), bipolar junction transistors, field effect transistors, programmable unijunction transistors, comparators, voltage regulators, operational amplifiers.

Electronic circuits may be included in the accessory device handpiece or in the plugs or wires associated with it. For example, the wire from the return plug can be routed to the power plug and one or more electronic circuits can be incorporated into the power plug. This approach allows the power wire and the return wire to both exit from the distal portion of the power plug as part of a single cable, a feature that can be particularly beneficial for bipolar applications where both wires need to be routed to the accessory handpiece.

Analogously, electronic circuits may be in the return plug if the power wire and any control wires are routed to the return plug. Incorporating circuits into the power plug, compared to placing the components in the handle, prevents any substantive increase in size or weight from inconveniencing the user. Similarly, placing circuit components in the plug will keep any heat that they may generate from heating the accessory handpiece and allow the plug to be designed with suitable heat sinks such as air flow holes or heat sinks such as extended surface features. The plug is also away from bodily fluids and solutions such as normal saline that may tend to penetrate and compromise circuit elements unless special precautions are taken. Such precautions may add size and weight to accessories and, consequently are not always desirable in components being held and manipulated by surgeons. If circuits are placed in the handle, fluid may flow through the handle, such as for aspiration or irrigation, and the fluid may be used to cool components or the handle.

Electronic circuits may be placed in locations other than one of the plugs. One or more circuits may also be placed along the cable between the plugs and the accessory. If it is desired, one or more circuits may also be incorporated into a module that plugs into the power output and return jacks of an electrosurgical generator. The module may have one or more output ports that connect to connectors for the accessory, return path device, or both. Such a module may be reusable or a single use device. Similarly, the accessory handpiece and return path device may be reusable or single use devices.

When electrosurgical energy is applied to the surgical site, an RF energy path exists between the power port, through conductive and other elements that carry RF power, through direct or indirect tissue contact, through tissue, and the return port. One of skill in the art will appreciate that features associated with the power port and return port connections may be interchanged because the RF energy is an alternating current.

The power port may be the monopolar output and the return port may be the monopolar return port. Using the monopolar ports may be desirable for use with some bipolar applications such as during arthroscopic ablation, where high power or high voltages are desired. For example, arthroscopic ablation using a general purpose electrosurgical generator can be facilitated using the coagulation, desiccation, or fulgurate mode because the high peak to peak voltages promote arc formation.

In other cases, the power and return ports may be bipolar outputs. These ports may be selected when lower power outputs are desired and/or when more controlled thermal tissue spread is desired, such as for neurosurgery or when collagen shrinkage is desired. Collagen shrinkage procedures may include arthroscopic or cosmetic surgery.

In any other embodiment optionally electrical power may be obtained using a power supply wire that extracts energy without connecting to the electrosurgical generator's power output. In these embodiments one or more conductive elements, such as one or more wires, act as at least one antenna or inductive pickups and connect to at least one terminal of the illumination means either directly or indirectly through one or more other conductors or electronic components. At least one other terminal of the illumination means is connected to the return port of the electrosurgical generator or other low potential point. One or more two terminal devices such as LEDs or neon lamps may be used as illumination means. In these options, by extracting energy without direct power connection to the electrosurgical generator power port, may advantageously extract power from the RF electromagnetic emissions and not interact with the output or input of the electrosurgical generator electronics or sensing systems associated with supplying RF power to the patient.

A common feature in any electrosurgical accessories is for one or more control wires to extend from the power plug and for those wires to electrically connect to one or more conductors or jacks in the generator. These control wires connect to one or more switches in the accessory, typically in the handpiece (handle), and allow the user to activate the generator to have the generator deliver power.

Another common optional feature is for the return path device in the form of a monopolar return electrode pad to have two wires leading from it to the return plug and for the return plug to connect to a connector or jack in the generator having two conductive contacts. The two conductive paths are used to implement features that measure the contact impedance between the return pad and the patient's skin to determine whether adequate contact exists to avoid unintentional burns where the return pad is applied to the skin. These additional conductive paths may be routed so that they pass through a single plug, such as the power plug, to reduce the number of cables leading to an accessory, such as a bipolar device.

In another option, a system for illuminating a surgical field or for facilitating treatment in a surgical field comprises an electrosurgical generator configured to provide radiofrequency power at an output voltage, voltage reduction means and an illumination element or other electrically activated device requiring power for operation. The voltage reduction means is electrically coupled with the electrosurgical generator and is configured to provide a second voltage different than the output voltage. The illumination element or other device is electrically coupled with the voltage reduction means, and the radiofrequency power from the electrosurgical generator energizes the illumination element or the other device and produces light for illuminating the surgical field or facilitates treatment in the surgical field. The illumination element or the other device is energized with the second voltage which is less than the output voltage.

In another option, a system for illuminating a surgical field or facilitating treatment in the surgical field, comprises an electrosurgical generator configured to provide radiofrequency power at an output voltage, rectifying means and an illumination element or other electrically activated device requiring power for operation. The rectifying means is electrically coupled with the electrosurgical generator and configured to receive the radiofrequency power and also configured to output rectified power which is direct current power. The illumination element or the other device is electrically coupled with the rectifying means and the rectified power energizes the illumination element or the other device and produces light for illuminating the surgical field or facilitates treatment in the surgical field.

In still another option, a system for illuminating a surgical field or facilitating treatment in the surgical field, comprises an electrosurgical generator configured to provide radiofrequency power at an output voltage, an output plug operably coupled with the electrosurgical generator, and a return electrode adapter operably coupled with the electrosurgical generator. The system also comprises a secondary power source disposed in the output plug or the return electrode adapter, an electrosurgery instrument having an illumination element for illuminating the surgical field or other electrically activated device requiring power for operation and configured to facilitate treatment in the surgical field, and a power conductor configured to carry power from the output plug to the illumination element or the other device.

In yet another option, a method for illuminating a surgical field or for facilitating treatment in the surgical field, comprises providing an electrosurgical generator that produces radiofrequency power at an output voltage and modifying the radiofrequency power. The method also comprises energizing an illumination element or other electrically activated device requiring power for operation, either being coupled to an electrosurgical instrument with the modified power, and illuminating the surgical field with light from the illumination element or facilitating treatment in the surgical field with the other device activated.

In another option, a system for illuminating or facilitating treatment in a surgical field comprises an electrosurgical generator configured to provide radiofrequency power at an output voltage and an illumination element or other electrically activated device requiring power for operation, and that is electrically coupled with the electrosurgical generator. The radiofrequency power from the electrosurgical generator energizes the illumination element or other device and produces light for illuminating the surgical field or facilitates treatment in the surgical field. The system also may include at least one multi-function actuatable switch, with each switch having a plurality of positions. In a first position of each switch, power is delivered to the illumination element or the other device so as to illuminate the surgical field or facilitate treatment in the surgical field, without current from the electrosurgical generator being delivered to tissue in the surgical field. In a second position of each switch, power is supplied to the illumination element or the other device so as to illuminate the surgical field or facilitate treatment in the surgical field, and simultaneously current from the electrosurgical generator is delivered to the tissue and the current is configured achieve a predetermined surgical effect, such as cutting, coagulation, ablation, or sealing, of the tissue.

In another option, a system for illuminating or facilitating treatment in a surgical field comprises an electrosurgical generator configured to provide radiofrequency power at an output voltage and an illumination element or other electrically activated device requiring power for operation, and that is electrically coupled with the electrosurgical generator. The radiofrequency power from the electrosurgical generator energizes the illumination element or other device and produces light for illuminating the surgical field or facilitates treatment in the surgical field. The system also includes a first and a second multi-function actuatable switch, with each switch having a plurality of positions. In a first position of the first switch, power is delivered to the illumination element or the other device so as to illuminate the surgical field or facilitate treatment in the surgical field, without current from the electrosurgical generator being delivered to tissue in the surgical field. In a second position of the first switch, power is supplied to the illumination element or the other device so as to illuminate the surgical field or facilitate treatment in the surgical field, and simultaneously current from the electrosurgical generator is delivered to the tissue and the current is configured to cut the tissue. In a first position of the second switch, power is delivered to the illumination element or the other device so as to illuminate the surgical field or facilitate treatment in the surgical field, without current from the electrosurgical generator being delivered to tissue in the surgical field. In a second position of the second switch, power is supplied to the illumination element or the other device so as to illuminate the surgical field or facilitate treatment in the surgical field, and simultaneously current from the electrosurgical generator is delivered to the tissue and the current is configured to coagulate the tissue.

In yet another option, a system for illuminating or facilitating treatment in a surgical field comprises an electrosurgical generator configured to provide radiofrequency power at an output voltage and an illumination element or other electrically activated device requiring power for operation, and that is electrically coupled with the electrosurgical generator. The radiofrequency power from the electrosurgical generator energizes the illumination element or other device and produces light for illuminating the surgical field or facilitates treatment in the surgical field. The system also has a plurality of switches, wherein actuation of a first switch delivers the power to the illumination element or the other device so as to illuminate the surgical field or facilitate treatment in the surgical field, without current from the electrosurgical generator being delivered to tissue in the surgical field. Actuation of a second switch delivers power to the illumination element or the other device so as to illuminate the surgical field or facilitate treatment in the surgical field, and simultaneously current from the electrosurgical generator is delivered to the tissue and the current is configured to cut the tissue. Actuation of a third switch delivers power to the illumination element or the other device so as to illuminate the surgical field or facilitate treatment in the surgical field, and simultaneously current from the electrosurgical generator is delivered to the tissue and the current is configured to coagulate the tissue.

Any of the options may further comprise a status indicator such as colored lights which indicate which mode of operation the system is in, e.g. cut, coagulation, and illumination only.

Some options of the method may comprise modifying the radiofrequency power by reducing the output voltage. Modifying the radiofrequency power may comprise rectifying the output voltage into direct current. The method may also comprise electrosurgically cutting or coagulating tissue with power from the radiofrequency generator while illuminating the surgical field or otherwise facilitating treatment in the surgical field. The method may comprise illuminating the surgical field or facilitating treatment in the surgical field without delivering current from the radiofrequency generator to tissue in the surgical field.

Any of the options may further comprise an electrosurgical instrument operably coupled with the electrosurgical generator, and the illumination element or the other device may be coupled to the electrosurgical instrument. The electrosurgical instrument may comprise a suction instrument or an electrosurgical pencil for cutting and coagulating tissue. The illumination element or the other device may be releasably coupled to the pencil or the suction instrument or other electrosurgical instrument. The illumination element or the other device may be coupled to a telescoping tube that is slidably coupled with a handle.

The illumination element may be configured to illuminate the surgical field or the other device may facilitate treatment in the surgical field when current provided by the electrosurgical generator is delivered to tissue in the surgical field. The illumination element may be configured to illuminate the surgical field or the other device may facilitate treatment in the surgical field when current provided by the electrosurgical generator is not delivered to tissue in the surgical field.

The voltage reduction means may comprise one or more components that produce a pulse width modulated output. The voltage reduction means may be responsive to at least one voltage output to produce voltage within a pre-specified voltage range.

Some options may further comprise rectifying means electrically coupled with the electrosurgical generator and configured to receive the radiofrequency power and configured to output rectified power. The rectified power may be direct current. The illumination element or the other device may be coupled with the rectifying means, and the rectified power may energize the illumination element and provide light for illuminating the surgical field or energize the other device and facilitate treatment in the surgical field. The rectifying means may comprise one or more diodes or a transformer. The voltage reduction means may supply the illumination voltage to the rectifying means. The other device may comprise a camera or a sensor.

Some embodiments may comprise voltage reduction means electrically coupled with the electrosurgical generator and configured to provide a second or more voltages. The illumination element or the other device may be electrically coupled with the voltage reduction means, and the radiofrequency power from the electrosurgical generator may energize the illumination element or the other device and produce light for illuminating the surgical field or for facilitating treatment in the surgical field. The illumination element or the other device may be energized at the second voltage and the second voltage may be less than the output voltage of the generator. One or more other voltages less than the voltage of the electrosurgical generator and different than the second voltage may energize additional means for treating tissue or otherwise facilitating treatment or diagnosis.

The voltage reduction means may comprise one or more components that produce a pulse width modulated output. The voltage reduction means may be responsive to at least one voltage output to produce voltage within a pre-specified voltage range. The voltage reduction means may supply the second voltage or more voltages to the rectifying means.

The voltage reduction means may comprise at least two passive electronic components arranged into a voltage divider. At least one of the passive electronic components may be a capacitor. Or at least three capacitors may be used, and the electrosurgical generator may comprise an active radiofrequency power connector and a return radiofrequency power connector. The at least three capacitors may be configured to redundantly block direct current to the active and return radiofrequency power going to patient tissues.

The system may further comprise an electrosurgical instrument operably coupled with the electrosurgical generator, and the illumination element or the other device may be coupled to the electrosurgical instrument. The electrosurgical instrument may comprise a suction instrument or an electrosurgical pencil for cutting and coagulating tissue. The illumination element or the other device may be releasably coupled to the suction instrument or the electrosurgical pencil.

The illumination element may be configured to illuminate the surgical field or the other device may facilitate treatment in the surgical field when current provided by the electrosurgical generator is delivered to tissue in the surgical field. The illumination element or the other device may be configured to illuminate the surgical field or facilitate treatment in the surgical field when current provided by the electrosurgical generator is not delivered to tissue in the surgical field. The other device may comprise a camera or sensor. The illumination element or the other device may be coupled to a telescoping tube which is slidably coupled with a handle or the electrosurgical instrument.

The secondary power source may store power provided by the electrosurgical generator. The secondary power source may comprise a battery or a capacitor.

The responsive voltage reduction means may use capacitors or reactive components and may use one or more switches to select between at least two current paths that produce different voltage reductions. Switching means may comprise at least two field effect transistors. Switch means control may include hysteresis control to avoid switches oscillating back and forth at a switch point.

The diodes used may have a reverse recovery time of less than about 2 microseconds or less than about 200 nanoseconds.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
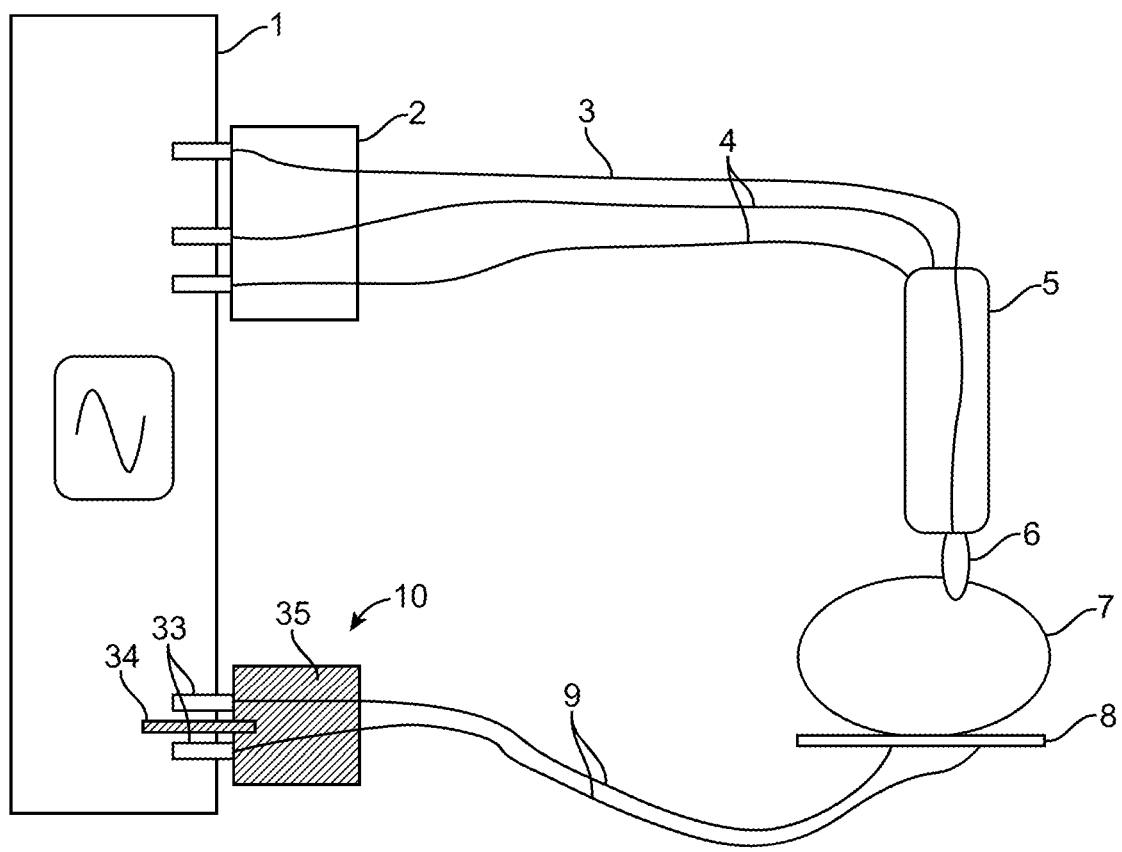
FIG. 1 illustrates a conventional monopolar electrosurgery system.

Specific embodiments of the disclosed device, delivery system, and method will now be described with reference to the drawings. Nothing in this detailed description is intended to imply that any particular component, feature, or step is essential to the invention.

The present invention will be described primarily in relation to an illuminated electrosurgical instrument. However, one of skill in the art will appreciate that this is not intended to be limiting, and the devices, systems and methods disclosed herein may be used in other applications and other anatomies. For example, instead of powering an illumination element such as an LED, any of the techniques described herein may be used to power any other device used during a surgical procedure such as a camera, a sensor, user feedback display, etc.

Electrosurgery.

Radiofrequency electrical power is frequently applied to surgical instruments to facilitate both cutting and coagulation during surgical procedures. The use of such electrically powered surgical instruments is generally referred to as electrosurgery. Electrosurgical techniques often use an instrument with working surfaces that contact tissue, such as a tissue ablation or cutting device, a source of radiofrequency (RF) electrical energy, and a return path device, commonly in the form of a return electrode pad (for monopolar electrosurgery) or a return electrode on the instrument (for bipolar electrosurgery). The working surfaces that contact the patient in the treatment region are commonly called the active electrodes or electrode. The return path device contacts the patient directly on the tissue or indirectly through, for example, a conductive liquid such as blood or normal saline. The return path device provides a return electrical path from the patient's tissue. Both the instrument and the return path device are connected using electrically conductive wires to the source of the radiofrequency electrical energy which serves as both the source and the sink for the electrical energy to produce a complete electrical circuit.

The conductive elements in or near the patient tissue are electrodes. Conventionally, the two electrodes are called the active and return electrodes in electrosurgery. When the instrument and the return path device are separate devices the technique is termed monopolar. In monopolar procedures the active electrode is smaller and focuses electrical energy on the target tissue and the return electrode is large and designed to provide a large return current path that does not affect the tissue. In some cases the instrument contains working surfaces that both supply the electrical energy and provide the return path. In these cases the technique is termed bipolar. Bipolar forceps are an example of such an instrument.

RF Generators.

The source of RF energy (the generator) has an output power that depends upon the characteristics of its design, including the design of its internal circuitry. Typically, the clinical user sets the generator to the output power desired. When the generator operates, the output power typically depends upon the impedance of the load into which the generator is delivering power. In general, the various generators available operate in modes that approximate constant voltage devices, constant power devices, or some hybrid mode that lies between constant voltage and constant power. The modes approximate constant voltage or constant power output due to the variations inherent in electronic component performance.

General purpose generators commonly used in operating rooms typically operate in a constant power mode when power outputs other than low power are desired. General purpose electrosurgical generators used for open surgical procedures may approximate either constant voltage or constant power devices. Generators used for some procedures, such as bipolar arthroscopic surgical procedures in which the active and return electrodes are submerged in a body cavity containing an electrically conductive liquid, generally operate as constant voltage sources to promote stable operation.

Generators provide waveforms that vary in voltage, frequency, and waveform pattern to suit the needs as determined by surgeons. The waveform produced is controlled by the surgeon and two broad categories, CUT (for cutting tissue mode) or COAG (for coagulation of tissue mode) are employed. The voltage amplitudes may vary from less than 100 volts to about 5,000 volts and cutting generally may require a minimum of about 300 volts. The frequency used varies depending upon the design of the generator and may range from about 100 kHz to over 1 MHZ, with typical general purpose generators operating between about 250 kHz and 750 kHz. The voltage waveforms vary from approximately sinusoidal, used for cutting, to periodic bursts of damped sinusoids, used for coagulation and also for cutting with coagulation. For example, a general purpose generator may produce a 500 kHz sinusoidal wave for pure cutting and a family of coagulation waveforms that have repetitive damped 500 kHz sinusoidal bursts having duty factors between about 25 and 50 percent with repetition rates of about 30 kHz. Any of these ranges of operating parameters may be used with any of the embodiments of electrosurgical devices, systems, and methods disclose herein.

General purpose generators typically have one or more connectors for monopolar instrument connections. These connections typically have three connectors. One connector supplies the RF power that leads via a wire to the handpiece and the other two connectors provide control connections via wires to switches in the handpiece. The control connections are to switches that active the CUT or COAG mode of the generator, as selected by the surgeon pressing the desired switch on the handpiece. The generator may also be controlled by actuating a footswitch.

General purpose generators also may have a connector for the return electrode for monopolar applications. The return connectors typically have two conductors to accommodate split pad return electrodes often used to provide a measure of the quality of the connection to the patient at the return electrode site. These connectors may employ a fixed nonconductive pin to signal the generator whether the return pad being employed has a split pad or a single pad. General purpose electrosurgical generators typically may have two connectors for bipolar accessory connections. In general purpose electrosurgical generators bipolar power is often controlled by a footswitch and therefore the handpiece may not have switches.

To date, surgical site illumination powered without optical cables leading to the instrument or using batteries in the surgical instrument held by the surgeon has not been available. Furthermore, surgical site illumination powered by the RF energy delivered by electrosurgical generators has not been available to surgeons. Providing such illumination using a general purpose electrosurgical generator by employing an accessory compatible with the range of voltages, frequencies, and waveforms employed during electrosurgery would be desirable.

Following conventional terminology, the radiofrequency power supply is preferably an electrosurgical generator and the device that connects to the electrosurgical generator to conduct power to the patient is the accessory. Accessories can be either single use devices that arrive sterile from the manufacturer or they can be cleaned, sterilized, and reused. Any of the features described herein and related to the RF generator may be used with any of the exemplary embodiment of electrosurgical devices, systems and method disclosed in this specification.

Monopolar Electrosurgery.

FIG. 1 illustrates a conventional monopolar electrosurgical system. Electrosurgical generator 1 accepts monopolar power connector plug 2 that is part of the accessory. Connector plug 2 has three conductors 3 and 4 that go from connector plug 2 to handpiece 5 (also called a handle) that is also part of the accessory. One of the conductors, the radiofrequency power conductor 3, carries the high voltage radiofrequency energy that will be applied to the patient's target tissue. The other two conductors act as signal control lines to the handpiece 4 and are connected to switches (not shown) in the handpiece 4. The switches are actuated by the surgeon and connect either one or the other of the signal control lines 4 to the radiofrequency power conductor 3 which completes a sense circuit (not shown) in the electrosurgical generator 1 that causes the electrosurgical generator 1 to send power to the radiofrequency power conductor 3. One of the signal control lines to the handpiece 4 is connected to a switch (not shown) that activates cut mode and the other signal control line to the handpiece 4 is connected to a switch (not shown) that activates coagulation mode. The radiofrequency power conductor 3 connects to active electrode 6 through handpiece 5.

FIG. 1 shows radiofrequency power conductor 3 as being continuous through handpiece 5. Radiofrequency power conductor 3 is conventionally routed through the accessory handpiece 5 and may connect to a variety of internal conductors (not shown) that eventually make electrical contact with the accessory active electrode 6, such as a blade. Active electrode 6 may be a blade, ball, loop, or other device that makes direct contact with patient target tissue or it may make indirect contact through a conductive liquid such as blood or normal saline or power may be conducted through sparks or arcs through a gas or vapor.

Both cut and coagulation mode produce radiofrequency high voltage output power that may have peak voltages ranging from about 250 volts to about 5,000 volts when predetermined surgical effects are produced, although some electrosurgical generators 1 may be set to produce voltages less than 250 volts, such as 50 volts or lower. The electrosurgical generator 1 has user accessible controls (not shown) such as buttons, switches, dials, and indicators that are used to set the power output and the type of cutting and coagulation mode to be used. Generator output voltage can vary over a wide range as the user accessible controls are adjusted. Generator output voltage can vary over a wide range during a fixed setting such as in generators designed to operate as constant power devices adjust the output voltage as the generator adjusts to changes in load impedance. A changing voltage may undesirably increase or decrease the intensity of light emitted from an illumination means, such as an LED, as electrosurgical output voltage changes. Additionally, the output power voltages may be much higher than can be used by conventional illumination devices such as light emitting diodes (LEDs). Therefore, the monopolar power supplied by the electrosurgical generator 1 may not always be directly used by conventional illumination devices. It is usually preferable to use a power source that maintains output voltage and current within predetermined ranges to supply the illumination element. Hence, the monopolar power supplied by electrosurgical generator 1 may need to have its voltage reduced, be rectified, or otherwise modified.

FIG. 1 further illustrates active electrode 6 contacting target tissue in patient 7. The electrical current flows from active electrode 6 through patient 7 and then to return electrode 8. Return electrode 8 can be a single conductor or it can be a split pad with two conductors (not shown) separated side by side with an insulating region (not shown) between them. FIG. 1 illustrates a two conductor return electrode 8 as can be seen by the two return power conductors 9. The return power conductors 9 (or single conductor or two conductors electrically connected if the return electrode 8 is a single conductor) go to a monopolar return electrode plug 10 that connects to electrosurgical generator 1 with return electrode pins electrically contacting conductors (not shown) in electrosurgical generator 1. Return electrode plug 10 has body 35 that has a solid split return pad indicator pin 34 extending from it when the return electrode 8 connected thereto has two electrode pads. Split return pad indicator pin 34 goes through a small hole (not shown) in electrosurgical generator 1 to activate features that monitor the quality of contact between return electrode 8 and patient 7. When return electrode 8 is not split into two conductors return electrode plug 10 does not have split return pad indicator pin 34.

Typically, the radiofrequency power conductor 3 and the signal control lines 4 are bundled into a single cable or cord. Similarly, the return power conductors 9 are typically bundled into a single cable or cord. The conductors 3, 9, and signal lines 4 are insulated and long enough to have handpiece 5 and return electrode 8 a suitable distance from electrosurgical generator 1.

FIG. 1 illustrates an accessory that has signal control lines 4 going to it so that the surgeon can activate electrosurgical generator 1 using switches (not shown) in handpiece 5. Electrosurgical generator 1 typically has an option for the surgeon to activate electrosurgical generator 1 using a footswitch (not shown) in which case signal control lines 4 are not needed and handpiece 5 does not have the aforementioned switches (not shown).

Any of the features disclosed above in relationship to a monopolar electrosurgical device, system, or method may be applied to any of the exemplary embodiments disclosed herein.

Bipolar Electrosurgery.

Figure 2:
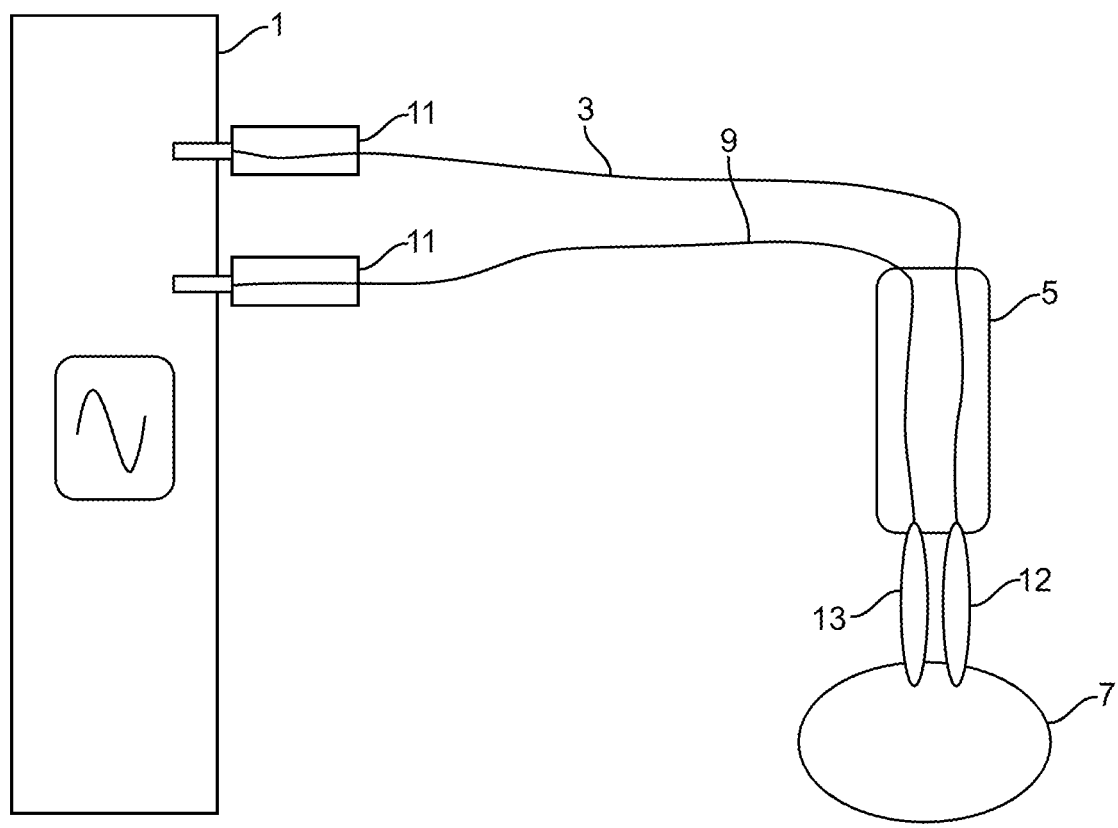
FIG. 2 illustrates a conventional bipolar electrosurgery system.

FIG. 2 illustrates a conventional bipolar electrosurgical configuration. Electrosurgical generator 1 accepts two bipolar connectors 11 that plug into electrosurgical generator 1. In some specialized electrosurgical generators the bipolar connectors 11 may be combined into a single housing. For general purpose electrosurgical generators the bipolar connectors 11 may be separate. One bipolar connector 11 connects to the radiofrequency power conductor that leads to the bipolar active electrode 12 through handpiece 5. The other bipolar connector 11 connects to return conductor 9 that leads to the bipolar return electrode 13 through handpiece 5. The bipolar active and return electrodes, 12 and 13, may have many configurations including being the tines of forceps or the electrodes at the distal tip of an arthroscopic surgical ablation instrument used in a submerged conductive liquid such as normal saline (not shown). Bipolar surgical accessories used with general purpose electrosurgical generators are typically activated using a footswitch (not shown) connected to electrosurgical generator 1 and bipolar handpieces used with general purpose electrosurgical generators do not usually have switches. The bipolar active and return electrodes, 12 and 13, both contact patient 7 either directly, as is the case with forceps, or may contact the patient indirectly, such as often occurs with the return electrode in bipolar arthroscopic ablation instruments submerged in normal saline (not shown).

As was the case for monopolar electrosurgery, users of bipolar electrosurgery can adjust the mode and power and power settings. Because the user is able to make adjustments to the output and is also able to select the mode, the output power voltage can vary over a wide range. Also, output power voltages may be much higher than can be used by conventional illumination devices such as light emitting diodes (LEDs). Therefore, the bipolar power supplied by electrosurgical generator 1 may not be able to be used by conventional illumination devices unless it is modified.

Any of the features disclosed above regarding bipolar electrosurgical systems may be used with any of the exemplary embodiments of illuminated electrosurgical systems disclosed herein.

Exemplary Illuminated Electrosurgical Systems.

For purposes of illustration, FIGS. 3 to 14 show how electrosurgical systems may be configured to implement an exemplary embodiment of an illuminated electrosurgical system. Without loss of generality, it is recognized that other embodiments besides those illustrated exist and can be derived from the principles illustrated in FIGS. 3 to 14 and the detailed description disclosed herein.

Figure 3:
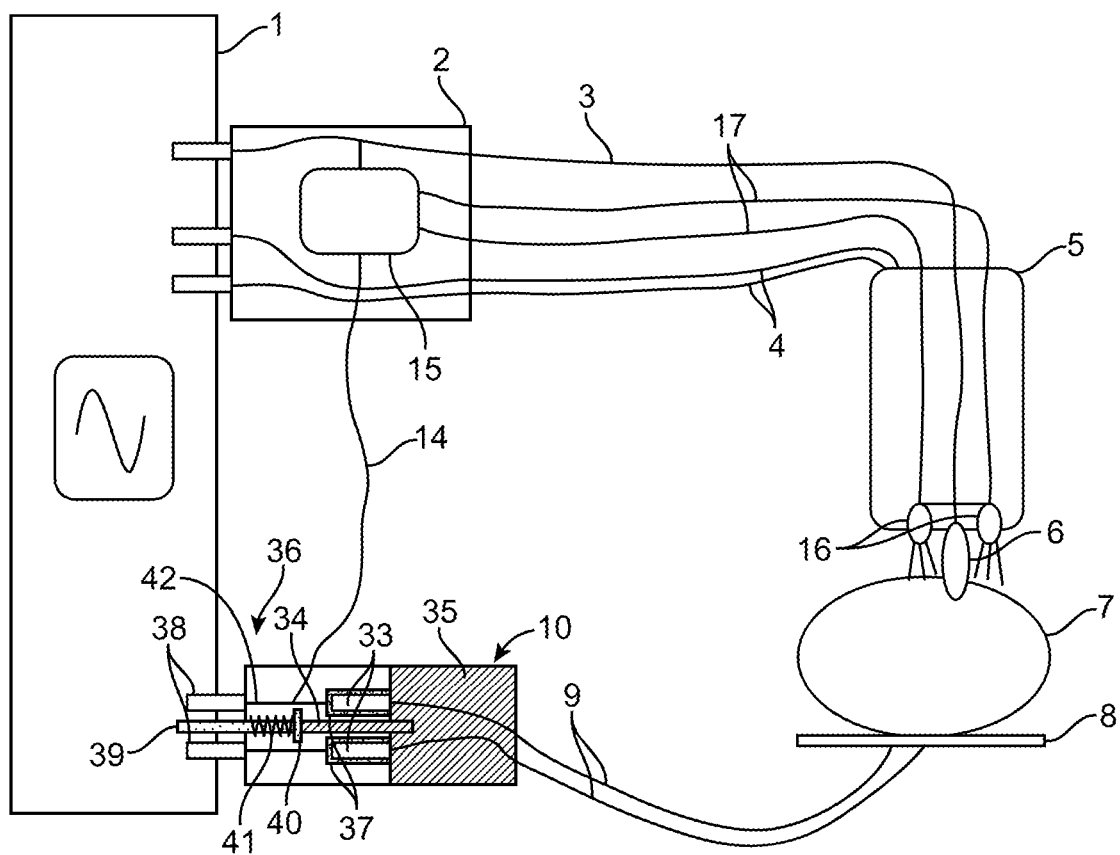
FIG. 3 illustrates illuminated monopolar electrosurgery with a radiofrequency power conversion module in the monopolar plug.

FIG. 3 illustrates an electrosurgical generator 1 set up for monopolar operation and also to extract radiofrequency (RF) electrical power from generator 1 for illumination. When electrosurgical generator 1 operates it outputs radiofrequency electrical power to radiofrequency power conductor 3. Power conversion means 15 extracts some of that power and converts it into power suitable for driving one or more illumination means 16 that produce photons that illuminate target tissue with visible light or non-visible light (e.g. infrared light) so that surgeons can see the surgical site or deliver light to the surgical site. Power conversion means 15 connects to radiofrequency power conductor 3 and supplemental return line 14 that connects to at least one of the return power conductors 9. Beneficially, supplemental return line 14 electrically connects to only one of the return power conductors 9 to avoid interfering with the control algorithms employed in electrosurgical generator 1 when using split return electrodes to monitor the quality of contact between return electrode 8 and patient 7. Power conversion means 15 converts the radiofrequency power from electrosurgical generator 1 into power suitable for driving at least one illumination means 16 that is connected to power conversion means 15 by illumination power conductors 17. Exemplary illumination means include LEDs, or any other source of light. Power conversion means 15 produces a voltage preferably less than the voltage difference between radiofrequency power conductor 3 and at least one of the return power conductors 9. The reduced voltage is compatible, possibly with further steps after voltage reduction, with driving the illumination means 16.

FIG. 3 illustrates two illumination means 16 connected in series although only one illumination means 16 may be used or more than two illumination means 16 may be used and multiple illumination means may be connected in series, parallel, or a combination of series and parallel. Illumination means 16 may be rigidly attached and be part of handpiece 16 or may be movable or detachable with flexible or moveable electrical connections to illumination power conductors 17. Illumination power conductors 17 are preferably single conductors and an alternative configuration is for multiple electrically conductive elements connected electrically in series or parallel or a combination of series and parallel to comprise one or more of illumination conductors 17.

Illumination means 16 may be selected to attach to or be part of handpiece 5 such that illumination means 16 does not make the size of handpiece 5 large or unwieldy or interfere with the surgeon's ability to observe the surgical area or access tissues of interest. Illumination means 16 may be any size, but preferably are smaller than approximately one inch in diameter and more preferably may be smaller than 0.5 inches in diameter and even more preferably may be about 0.39 inches (approximately 10 mm) in diameter or smaller and even more preferably may be about 0.2 inches (approximately 5 mm) in diameter or smaller and even more preferably may be about 0.08 inches (approximately 2 mm) in diameter or smaller. Illumination means 16 may preferably have a minimum dimension (diameter, width, length, or height) larger than about 0.01 inches in diameter. Illumination means 16 may have a cross-sectional area (the cross-sectional area of the illumination source itself) approximately parallel with a plane being illuminated by illumination means 16 that is preferably less than about 3 square inches and more preferably may be smaller than 0.2 square inches and even more preferably may be about 0.12 square inches or smaller and even more preferably may be about 0.03 square inches or smaller and still more preferably may be about 0.005 square inches or smaller.

Illumination means 16 may be a source of photons with at least a portion of the photons being at least part of the visible spectrum seen by humans such as an incandescent lamp, gas discharge lamp, a light emitting diode (LED), laser diode, or any other illumination element, although other photon sources are within the scope of the present invention such as fluorescent light sources, or polarized light, etc. Illumination source 16 may be a source of photons that has at least a portion outside of the visible spectrum of human beings but detectable by instruments that may be used to diagnose or treat diseases or provide other clinically significant benefits or provide clinical differentiation of tissues or organisms. For example, illumination source 16 may produce photons in the ultraviolet, near infrared, or infrared regions of the electromagnetic spectrum. One or more of illumination sources 16 may provide a range of photon frequencies such as in the range visible to humans and also in regions outside of the spectrum visible to human beings such as in the infrared, near infrared, or ultraviolet regions. The one or more illumination sources 16 may produce light that has a spectral composition characterized by what is commonly referred to as white light. Such white light sources may include one or more LEDs. An example of an LED that may be used is Cree C512A manufactured by Cree, Inc. of Durham, N.C. Pulsed LEDs may also be used. In addition to an illumination element, or in combination therewith, other powered elements such as cameras, sensors, or any other element requiring power may be powered using any of the techniques in this or other embodiments disclosed herein.

In other embodiments, the device or system may also include a polarizing filter or a light source that provides polarized light. Filters may also be used with the system in order to provide a specific wavelength of light or otherwise to provide light with specific characteristics.

As described herein, illumination sources 16 may be one or more LEDs. A LED may be a single light emitting diode or it may be an array of light emitting diodes in an assembly, possibly obtained from a vendor fabricated into the assembly. An example of such an LED array is the CXA 1310 LED array sold by Cree, Inc. The CXA 1310 LED array has about a 0.24 inch diameter (6 mm) optical source. Multi-colored LEDs may also be used, such as a red-green-blue RGB LED.

Illumination source 16 may be a composite of a photon source, such as an LED, and a light conveying medium that accepts photons in one portion and directs light to another portion of the conveying medium from which light is emitted to at least one clinically significant region, such as the target tissue to be illuminated. The light conveying medium may be selected because of differences in at least one index of refraction between components of the medium or between the medium and at least one surrounding material, such as air or normal saline or a material in handpiece 5, with at least some difference in index of refraction causing light to be at least partially guided from the photon source to at least one region of clinical significance to be illuminated.

The illumination power conversion means 15 and illumination source 16 may together consume sufficiently low power that the total power used for illumination is about 75 percent or less of the total power output of the generator. In still other embodiments, the fraction of total power used for illumination may be about 50 percent or less of the total power output of the generator or the fraction of total power used for illumination used may about 25 percent or less of the total power output of the generator. In other embodiments, the fraction of total power used for illumination used may be about 10 percent or less of the total power output of the generator. For example, the total power used for illumination may by about 10 watts which is less than about 20 percent of the power output of a generator set at about 50 watts or the power used may be about 2 watts which is less than about 5 percent of the power output from a generator set at about 40 watts.

Monopolar return connector plug 10, which is part of the return electrode pad assembly that includes electrode pad 8 and return power conductors 9, plugs into return pad adapter 36 that is part of some exemplary embodiments of the illuminated electrosurgical system. Return pad adapter 36 accepts return electrode pins 33 of the return connector plug 10 into return pad pin connectors 37. Return pad pin connectors 37 may be, for example, conductive metal tubes that have a friction fit with return electrode pins 33, possibly by using conductive metal tubes with an irregular shape or other features (not shown) such as ball detents or protrusions to induce a friction fit. Return pad pin connectors 37 connect to return pad adapter pins 38 through return pad adapter internal conductors 42. Return pad adapter pins 38 have substantially the same size and shape as used for return electrode pins 33 and insert into and connect to electrosurgical generator 1 in substantially the same manner as return electrode pins 33.

Supplemental return line 14 connects to one or more return pad adapter internal connectors 42 to allow a complete electrical circuit for supplying radiofrequency electrical power to power conversion means 15.

As shown in FIG. 3, power conversion means 15 connects electrically between radiofrequency power conductor 3 that is connected to handpiece 5 and at least one of return power connectors 9. Therefore, power conversion means 15 is electrically connected between the monopolar output and the monopolar return of electrosurgical generator 1. Power conversion means 15 may also be electrically connected between the bipolar output and return of electrosurgical generator 1, as will be described in more detail below.

Return pad adapter 36 has split return pad indicator extension pin 39 that is held inside return pad adapter 36 by the action of extension pin return spring 41 pushing against spring capture feature 40 that is part of indicator extension pin 39. For example, indicator extension pin 39 may be shaped somewhat like an ordinary construction nail with the nail head being spring capture feature 40. Extension pin return spring 41 is a spring such as a compression spring that pushes indicator extension pin 39 into return pad adapter 36 unless split return pad indicator pin 34 from a return connector plug 10 pushes against indicator extension pin 39. When a return connector plug 10 with a split return pad indicator pin 34 is inserted into return pad adapter 36 the split return pad indicator pin 34 passes through a small hole (not shown) in return pad adapter 36 and contacts indicator extension pin 39 and forces indicator extension pin 39 out of return pad adapter 36 such that indicator extension pin 39 goes into electrosurgical generator 1 in the same manner as occurs when a split return pad indicator pin 34 goes into an electrosurgical generator 1. The length and dimensions of indicator extension pin 39 may be the same as those used for split return pad indicator pins and are known to those skilled in the art of electrosurgical accessory design.

When return connector plug 10 does not have a split return pad indicator pin 34 then extension pin return spring 41 keeps indicator extension pin 39 inside return pad adapter 36. This example of split return pad indicator extension spring 39 and its operation used a compression spring such as extension pin return spring 41, as the means of keeping indicator extension pin return spring 41 in a state where it is inside of return pad adapter 36 unless return pad adapter 36 connects to return plug adapter 10 with a split return pad indicator pin 34. Return pad adapter 36 may be a device that connects to the monopolar return of an electrosurgical generator such that a monopolar return electrode plug can electrically and mechanically interface with the adapter to transfer electrical power and the mechanical indication of the presence of a split pad return electrode through the action of an indicator pin. Means for keeping indicator extension pin 39 inside return pad adapter 36 other than compression springs are within the scope of the invention and include, for example, elastomeric materials or features that are part of return pad adapter 36 or that are part of indicator extension pin 39.

Return pad adapter 36 may beneficially be made from a non-electrically conductive material such as a polymer except for the conductive elements and possibly extension pin return means, such as indicator extension pin return spring 41. FIG. 3 shows power conversion means 15 in the monopolar power connector plug 2 that connects to electrosurgical generator 1.

Figure 4:
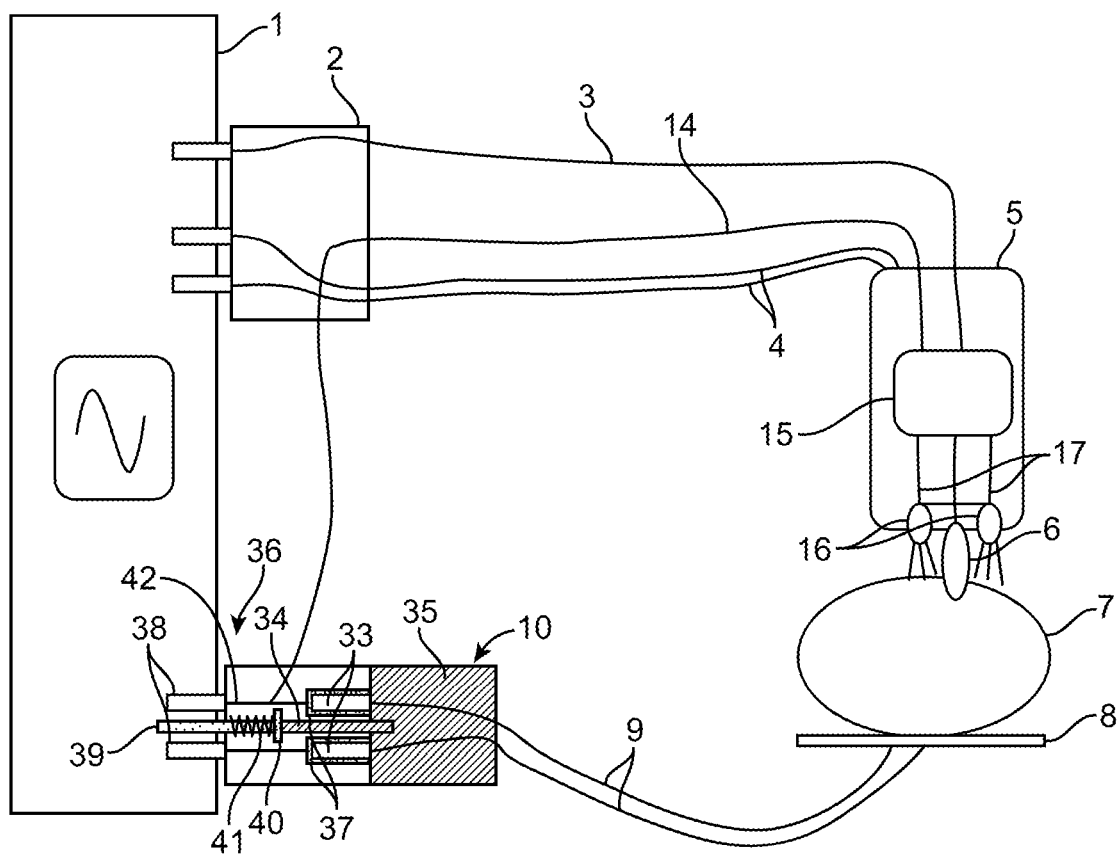
FIG. 4 illustrates illuminated monopolar electrosurgery with a radiofrequency power conversion module in the handpiece.
Figure 5:
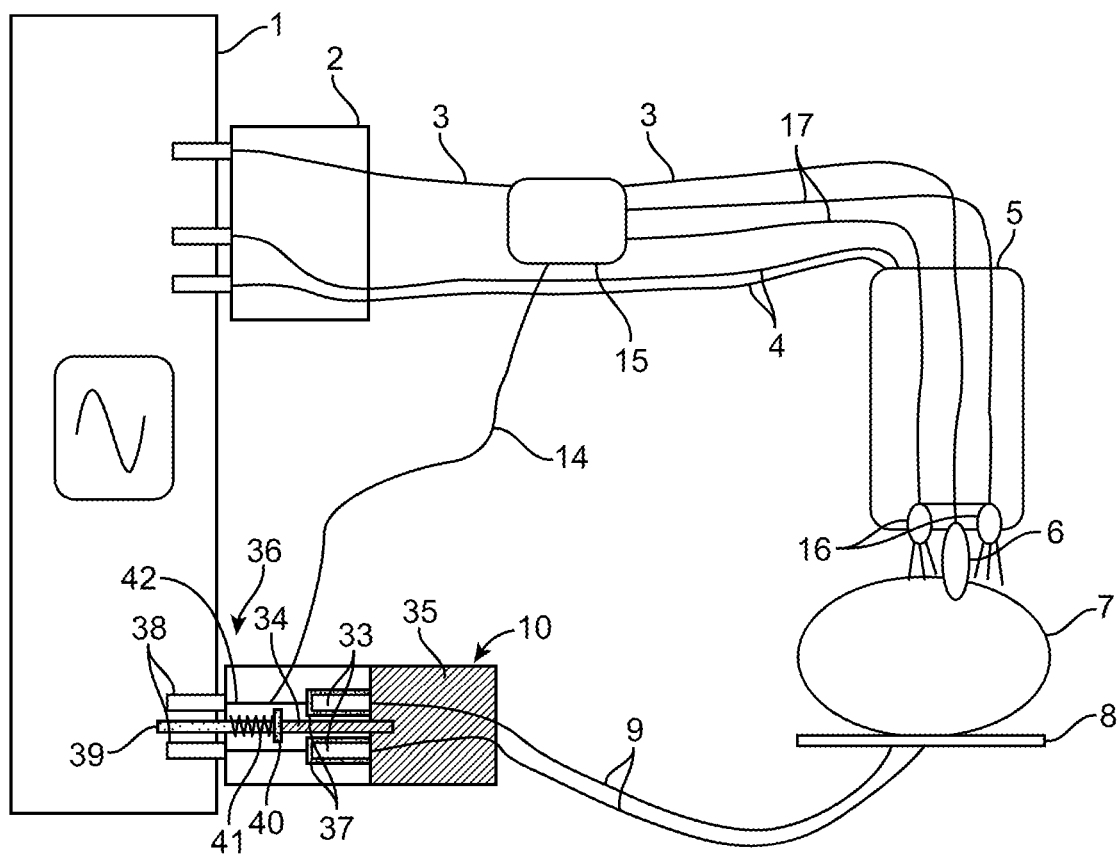
FIG. 5 illustrates illuminated monopolar electrosurgery with a radiofrequency power conversion module in a cable pendant.

FIG. 4 illustrates the power conversion means 15 in the handpiece 5 and FIG. 5 illustrates the power conversion means 15 in a cable pendant. It is also possible to have some elements of power conversion means 15 in more than one location. For example, part of the power conversion means may be located in the monopolar power connector plug 2 and another part in handpiece 5. Having power conversion means 15 in the monopolar power connector 2 or in pendant as shown in FIG. 5 compared to in handle 5 keeps the size and weight of handle 5 smaller than when power conversion means 15 is in handle 5. Smaller size and weight can make manipulating handpiece (handle) 5 easier and reduces the possibility of blocking the surgeon's view of tissues of interest.

FIGS. 3, 4, and 5 show conductors and lines 3, 4, 14, 17 going to handle 5. These conductors and wires may be bundled together in a cable or cord to reduce clutter and the possibility of tangling. Similarly, supplemental return line 14 shown in FIG. 5 may be routed through monopolar connector plug 2 and then to the pendant mounted power conversion means 15 rather than directly to power conversion means 15 as shown in FIG. 5.

This exemplary embodiment of electrosurgical system includes making part of the electrical return path pass through the output connector plug 3, as shown in FIG. 4. A supplemental return line 14 extends from the return adapter pad adapter 36 to the monopolar power connector plug 2. The supplemental return line 14 may be long enough to span the distance between the output connector (not shown) in electrosurgical generator 1 into which monopolar power connector plug 2 is plugged and the return connector (not shown) in electrosurgical generator 1 into which return adapter pad adapter plug 36 is plugged. This allows the user enough slack to conveniently connect monopolar power connector plug 2 and the return adapter pad adapter plug 36 to generator 1.

Monopolar power connector plug 2 with one or more components that are part of power conversion means 15 may be whatever shape or design is appropriate to enclose and protect the parts that it contains. Possible implementations may include overmolding, joining housing parts using ultrasonic welding or adhesives or mechanical fasteners such as screws. The design may include features to cool electronic components. These features may include holes or fins to promote air flow. The design may be made in whole or part from metal or other substance or substances that promote heat transfer. One embodiment is to mold housings with suitable spaces to hold the components after they have been fabricated into subassemblies. Sliding penetrating connectors of types familiar to those skilled in the art may then be used to make connections.

Figure 6:
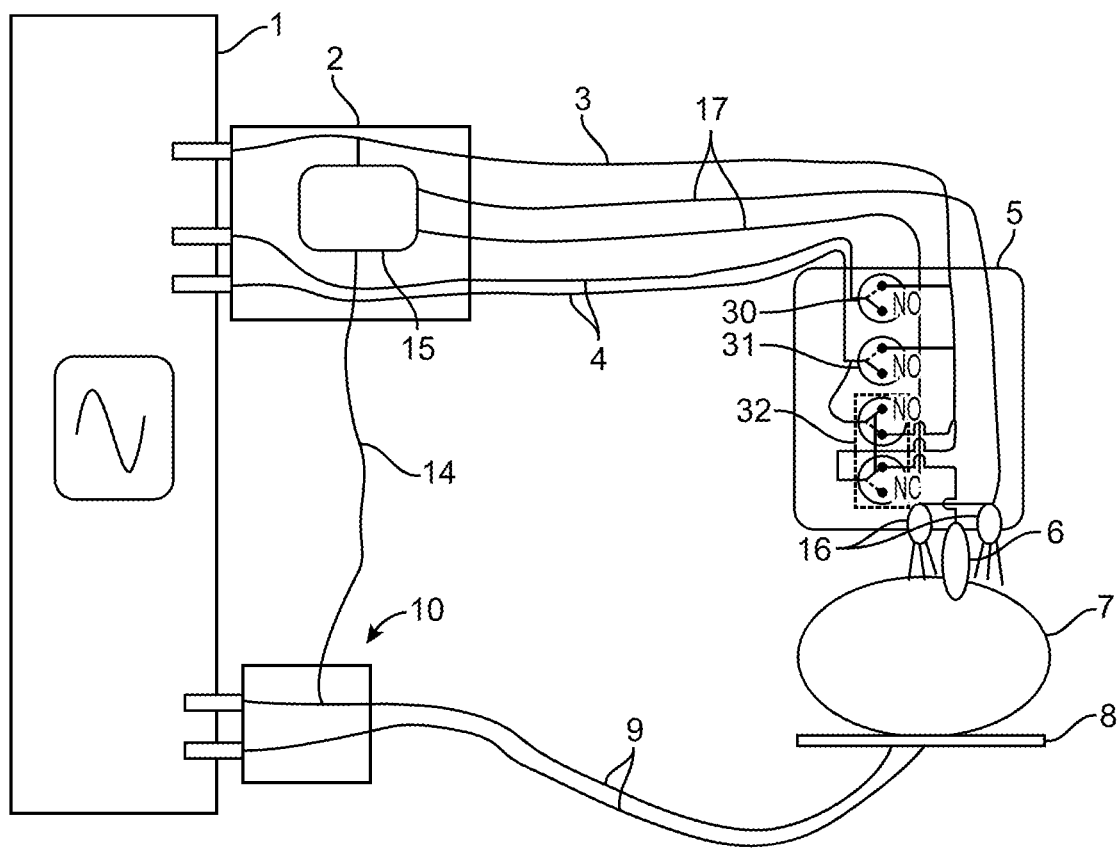
FIG. 6 illustrates illuminated monopolar electrosurgery with a third switch that allows using radiofrequency power for illumination without supplying radiofrequency power to the patient.

FIG. 6 illustrates a variation of the monopolar configurations disclosed in FIGS. 3 to 5 which employs only switch 32. FIG. 6 also shows switches 31 and 32 that, when activated, connect signal control lines 4 to radiofrequency power conductor 3. Such connections for typical electrosurgical generators 1 cause either cut or coag power to be delivered by electrosurgical generator 1. As seen in the figure, switches 31 and 32 are typically normally open (NO). Illumination only switch 32 is a double pole single throw switch with one pole configured to connect one of the signal control lines 4 to radiofrequency power conductor 3 while simultaneously disconnecting radiofrequency power conductor 3 from active electrode 6. The pole in switch 32 that connects the signal control line 4 to radiofrequency power conductor 3 is typically normally open (NO) and the pole that connects radiofrequency power conductor 3 to active electrode 6 is typically normally closed (NC). The poles of switch 32 are not closed at the same time. Activating switch 32 causes radiofrequency power conductor 3 to electrically connect one of the signal control lines 4 to radiofrequency power conductor 3 and that activates electrosurgical generator 1. Activation provides power to power conversion means 15 which powers one or more illuminations means 16. Activating illumination only switch 32 also disconnects radiofrequency power conductor 3 from active electrode 16. The result of activating the double pole single throw switch 32 is to activate electrosurgical generator 1 to power illumination means 16 without supplying power to active electrode 16. In one embodiment the pole that opens the connection to active electrode 16 opens before the pole that closes the connection between signal control line 4 and radiofrequency power conductor 3. This sequence keeps power from being applied to patient 7 when illumination only is selected as switch 32 is activated.

Figure 7:
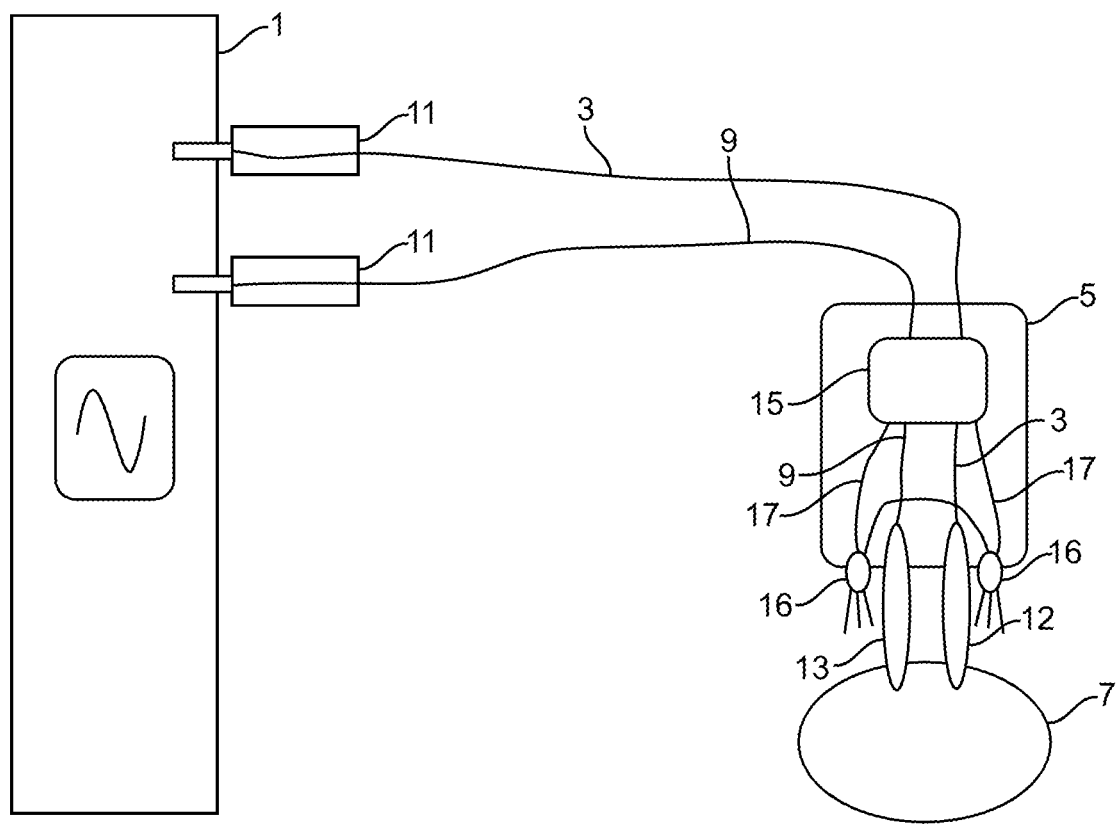
FIG. 7 illustrates illuminated bipolar electrosurgery with a radiofrequency power conversion module in the handpiece.
Figure 8:
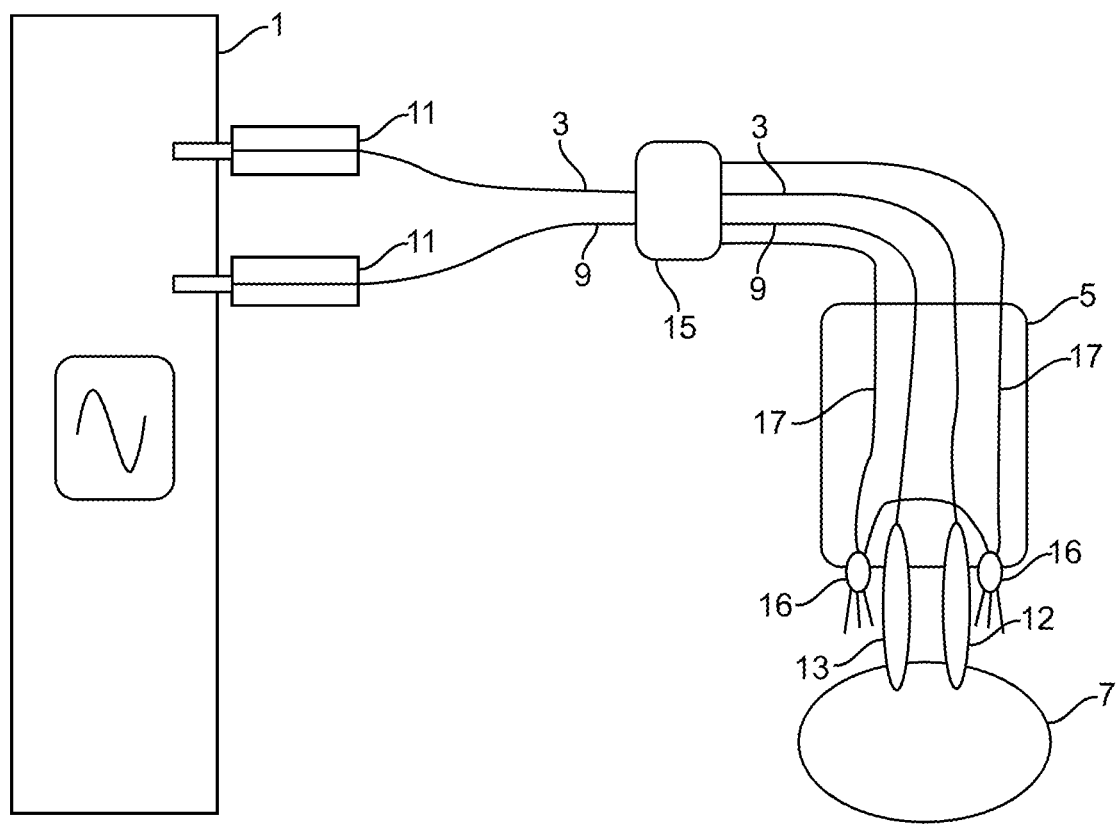
FIG. 8 illustrates an exemplary illuminated bipolar electrosurgery system with a radiofrequency power conversion module in a cable pendant.

FIGS. 7 and 8 illustrate exemplary embodiments configured for use with bipolar outputs of electrosurgical generator 1. As described earlier, bipolar output power of conventional electrosurgical generators is typically controlled by a footswitch (not shown) so the bipolar configurations illustrated in FIGS. 7 and 8 do not have signal control lines 4 seen in FIGS. 3, 4, and 5. FIG. 7 shows power conversion means 15 in handpiece 5 and FIG. 8 shows power conversion means 15 in a pendant. Having power conversion means 15 in a pendant reduces the size and weight of handpiece 5 compared to having power conversion means 15 in handpiece 5. Conductors and lines 3, 9, and 17 may be advantageously bundled in a cord or cable.

Figure 9:
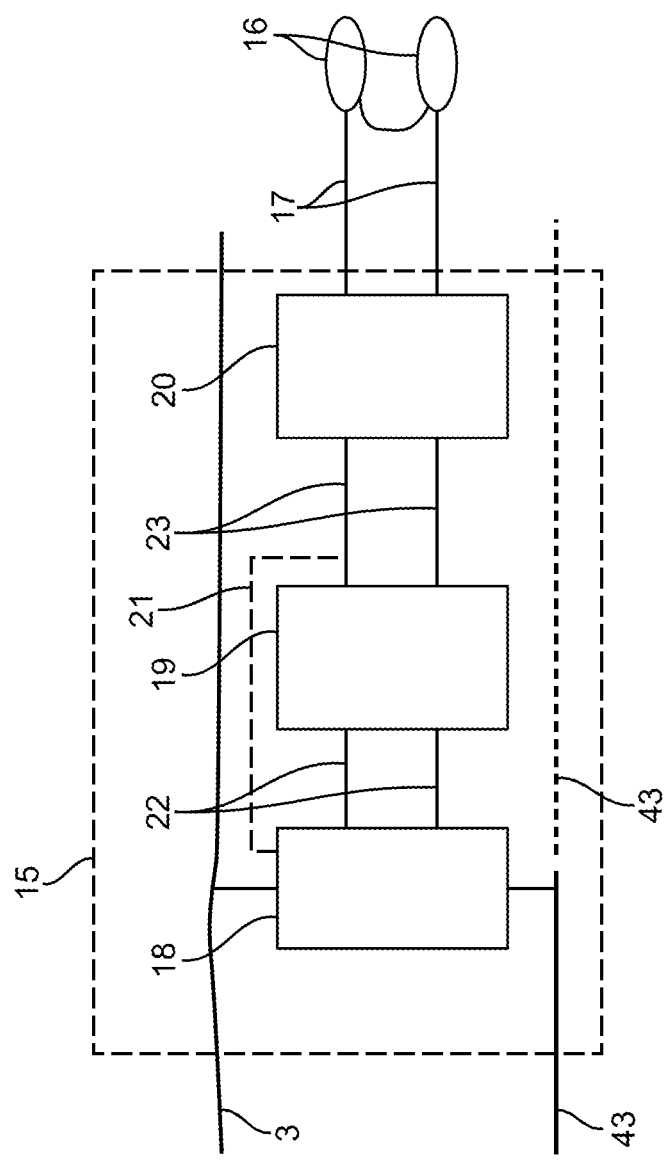
FIG. 9 is a block diagram of an exemplary power conversion means.

FIG. 9 illustrates a block diagram of an exemplary embodiment of power conversion means 15. Power conversion means 15 may comprise one or more of voltage reduction means 18, rectification means 19, and control or regulation means 20. As mentioned above, one or more of the one or more voltage reduction means 18, rectification means 19, and control or regulation means 20 may be located in the same place, such as in the monopolar power connector plug 2 or they may be located in more than one location such as in the monopolar power connector plug 2 and either in a pendant as shown in FIG. 5 or in handpiece 5. Alternative configurations are possible. For example, rectification means 19 may precede voltage reduction means 18. Another exemplary configuration may have two voltage reduction means 18, one on each side of rectification means 19 and either have, or not have, control or regulation means 20. Alternatively, control or regulation means 20 may provide control or regulation of voltage reduction to control any parameter such as current provided to one or more illumination means 16, such as LEDs.

FIG. 9 illustrates radiofrequency power conductor 3 passing through power conversion means 15 and electrically connected to voltage reduction means 18. Radiofrequency power conductor 3 may be connected to any part of power conversion means 15 such as the rectification means 19 if using an alternative configuration in which rectification means 19 precedes voltage reduction means 18. FIG. 9 illustrates that power conversion means 15 (and possibly in conjunction with FIGS. 3 to 8) is in parallel with the radiofrequency power supplied to patient 7 and thus, can supply power to one or more illumination means 16 whether or not electrosurgical power is being applied to patient 7. Therefore, whenever electrosurgical generator 1 is activated power will be supplied to one or more illumination means 16 whether or not active electrode 6 is contacting patient 7.

FIG. 9 illustrates two exemplary connections with general return power conductor 43. General return power conductor 43 is any conductor that is electrically connected to the return radiofrequency power of electrosurgical generator 1 and may be, for example, supplemental return line 14 shown in FIGS. 3, 4, and 5 for monopolar applications or return power conductor 9 for bipolar applications as shown in FIGS. 7 and 8. General return power conductor 43 may terminate in power conversion means 15, as shown in FIG. 9 by the solid portion of general return power conductor 43, as will commonly be the case for monopolar electrosurgical accessories such as those illustrated in FIGS. 3 to 5. General return power conductor 43 may continue to other parts of the electrosurgical accessory, as shown by the dashed portion of general return power conductor 43 in FIG. 9, such as in the bipolar electrosurgical accessories as illustrated in FIGS. 7 and 8.

Voltage reduction means 18 reduces the voltage difference between radiofrequency power conductor 3 and general return power conductor 43. The peak voltage difference between radiofrequency power conductor 3 and general return power conductor 43 may be greater than 100 volts and during cutting electrosurgical activities may exceed 300 volts and may be as high as 5,000 volts or more. Voltage reduction means 18 may reduce the voltage to preferably about one-half or less of the voltage difference between radiofrequency power conductor 3 and general return power conductor 43.

In other embodiments, voltage reduction means 18 may have a voltage reduction ratio that reduces the voltage to preferably about one-tenth ($1/10$) or less of the voltage difference between radiofrequency power conductor 3 and general return power conductor 43. As another alternative embodiment, voltage reduction means 18 may have a voltage reduction ratio that reduces the voltage to preferably about one-one hundredth ($1/100$) or less of the voltage difference between radiofrequency power conductor 3 and general return power conductor 43. As yet another alternative, voltage reduction means 18 may have a voltage reduction ratio that preferably reduces the voltage to preferably about one five-hundredth ($1/500$) or less of the voltage difference between radiofrequency power conductor 3 and general return power conductor 43. The output voltage of voltage reduction means 18 may be preferably in the range of 1 to 50 volts, or more preferably be in the range of 3 to 30 volts, or even more preferably be in the range 5 to 20 volts, or still more preferably be in the range of 5 to 12 volts.

The operation of voltage reduction means 18 may be responsive to the input voltage difference between radiofrequency power conductor 3 and general return power conductor 43 so that the voltage reduction ratio varies to produce an output voltage that is within a predetermined range, such as the output voltage ranges presented above.

The operation of voltage reduction means 18 may be responsive to a reduced voltage or other electrical characteristic detected in voltage reduction means 18 or to a reduced voltage or other electrical characteristic detected after voltage reduction means 18. FIG. 9 illustrates obtaining such downstream electrical characteristic using electrical characteristic feedback conductor 21 that connects to at least one of the conductors 23 between rectification means 19 and control and regulation means 20. For example, electrical characteristic feedback conductor 21 could convey a voltage to voltage reduction means 18 that voltage reduction means 18 uses to alter the voltage reduction ratio to produce an output voltage that is within a predetermined range, such as the output voltage ranges presented above.

Any of the embodiments described in this specification may also have a temperature sensor such as a thermocouple or thermistor that monitors temperature in the handle or any part of the electrosurgical instrument. Temperature monitoring may be useful for controlling LED performance which can drift over varying temperatures. If the temperature sensor requires power, it may be powered with the electrosurgical generator using any of the techniques described herein.

Alternative Power Means.

Figure 10:
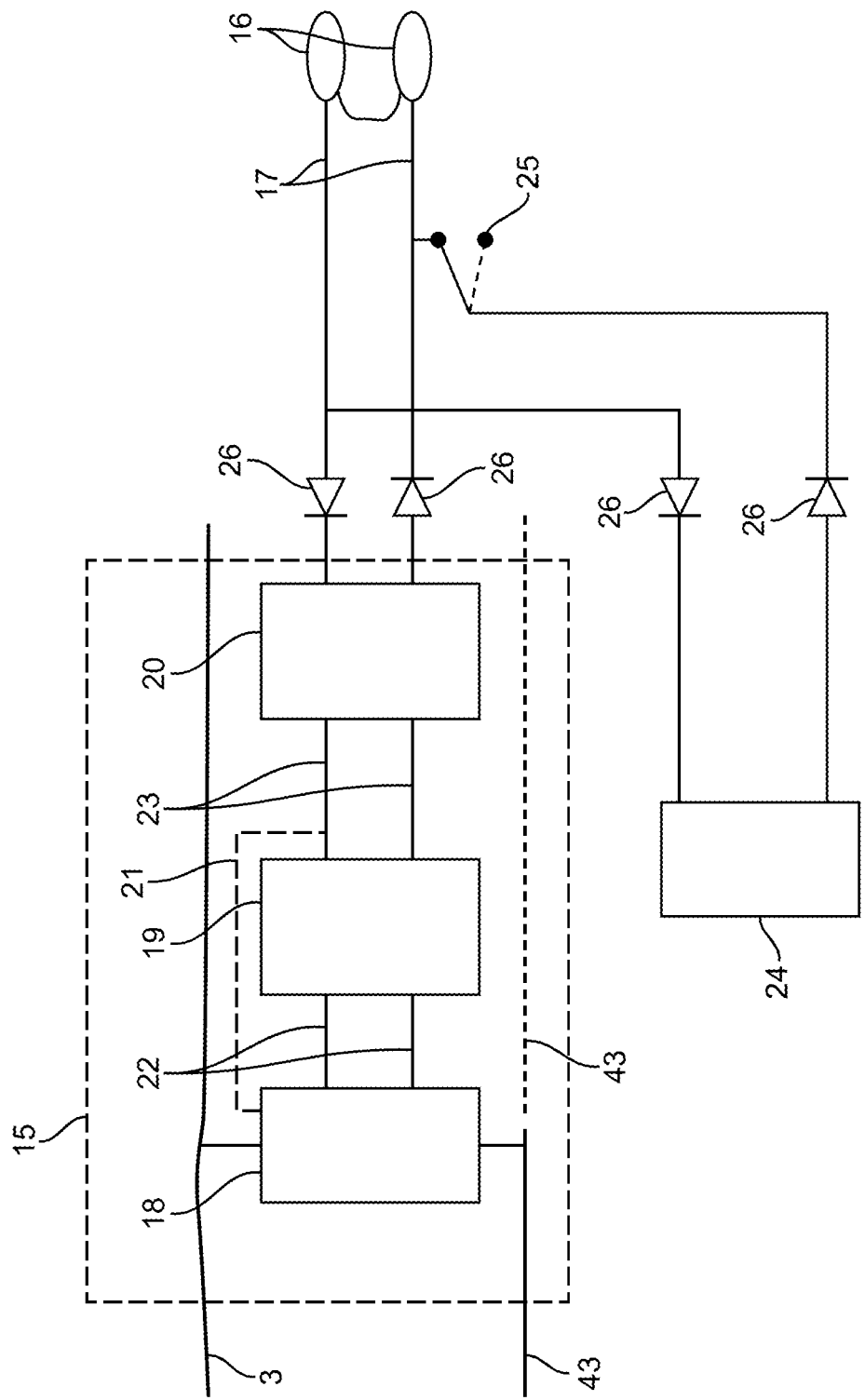
FIG. 10 is a block diagram of an exemplary power conversion means and an alternate power means.

FIG. 10 illustrates powering one or more illumination means 16 using power conversion means 15 with an alternative power means 24. This embodiment powers one or more illumination means 16 using either power conversion means 15 or alternative power means 24. For example, if electrosurgical power is present on radiofrequency power conductor 3 and general return conductor 43 then one or more illumination means 16 will be powered. This may occur whenever the user has activated an electrosurgical generator to produce either cut or coagulation power, whether or not tissue is being contacted by an active electrode. In the case where the user wishes to power one or more illumination means 16 without activating an electrosurgical generator to supply radiofrequency power conductor 3 and general return conductor 43 the user can activate switch 25 to have alternative power means 24 supply power to one or more illumination means 16. Current control means 26, such as diodes, may be employed to isolate or protect alternative power means 24 or power conversion means 15 from one another. Current control means 26 is illustrated as being single components on each line but current control means 26 may be circuits with multiple components including active components, such as diodes, transistors of various types, operational amplifiers, comparators, or voltage regulators, and passive components such as capacitors, resistors, or inductors.

Another option is similar to the configuration in FIG. 10 but with only alternative power means 24 and not using power conversion means 15. In the embodiment where only alternative power means 24 exists for illumination power when no control switches in the handpiece 5 exist for activating an electrosurgical generator (FIG. 7 for bipolar without any signal control lines 4 compared to FIG. 3 with monopolar and having switches that use signal control lines 4 to control electrosurgical generator 1) switch 25 would be the only switch needed to control illumination. In the embodiment where only alternative power means 24 exists for illumination power and control switches exist in the handpiece 5 for activating an electrosurgical generator (FIG. 3 with monopolar and having switches that use signal control lines 4 to control electrosurgical generator 1) switch 25 could be present to control illumination when the user does not want to activate electrosurgical generator 1 and additional double pole switches may be used to activate cut or coagulation while also closing circuits in parallel to switch 25 so that power is supplied to one or more illumination sources 16. This exemplary embodiment is described in more detail later.

Either with or without power conversion means 15 the alternative power means 24 may be located in handpiece 5 (such as how power conversion means is located in FIGS. 4 and 7), in a pendant (such as how power conversion means is located in FIGS. 5 and 8), or in a monopolar power conductor plug (such as how power conversion means is located in FIG. 3). Locating alternative power means 24 other than in handpiece 5 provides the advantage of reducing the size and weight of the handpiece.

Alternative power means 24 may be any power source that functions when electrosurgical generator 1 is not activated. For example, alternative power means 24 may be one or more of storage means that use chemical energy storage means such as batteries or fuel cells, storage means initially charged by energy from electrosurgical generator 1 such as capacitors. Other power means may include photovoltaic or other conversion devices that collect energy from the environment such as overhead surgical lighting, mechanical movement, or environmental electromagnetic energy. In the case of a capacitor, the capacitor will be charged with energy provided by the electrosurgical generator. The capacitor may be continuously charged when the electrosurgical instrument is operated in CUT or COAG mode, or it may be charged when current is not being delivered to the tissue. An example of a capacitor being charged is the filter capacitor C4 in FIG. 13. The capacitor size and voltage operating range can be selected after selecting the operating time and using the relationship that the usable energy stored is given by $E=1/2C*(V_s^2-V_f^2)$ where C is the capacitance in farads and $V_s$ and $V_f$ are the starting and final capacitor voltages and using methods known to those skilled in the art of electronics design using LED power requirements.

Voltage Reduction Means.

Figure 12:
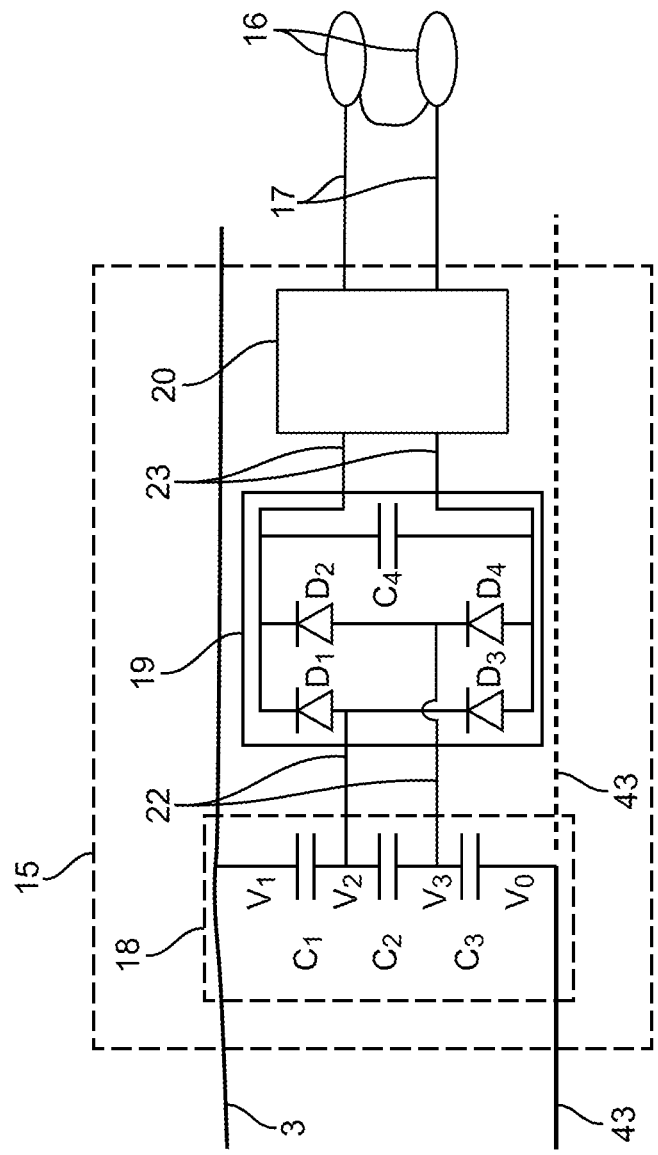
FIG. 12 illustrates an exemplary schematic of voltage reduction, rectification and control means.

FIG. 12 illustrates an exemplary embodiment that uses multiple passive components, $C_1$, $C_2$, $C_3$, to form a voltage divider for voltage reduction means 18. Passive components, $C_1$, $C_2$, $C_3$ may be fundamentally dissipative devices such as resistors or they may be fundamentally non-dissipative devices such as capacitors or even inductors. Employing fundamentally non-dissipative devices, such as capacitors, reduces energy losses and helps keep power conversion means 15 from heating along with whatever housing it is in such as monopolar power connector plug 2. Capacitors are well suited because of their cost and the impedance characteristics with radiofrequency power sources that are known to those skilled in the art.

A beneficial embodiment of the voltage divider is to have at least one capacitor between the radiofrequency power conductor 3 and the general return conductor 43 and the conductors to other parts of power conversion means 22 such as to rectification means 19 to provide direct current isolation between power conversion means 15 and radiofrequency power conductor 3 and the general return conductor 43, which may be a significant patient safety consideration. FIG. 12 illustrates such direct current isolation with $C_1$ and $C_3$ being the isolating capacitors.

Figure 11:
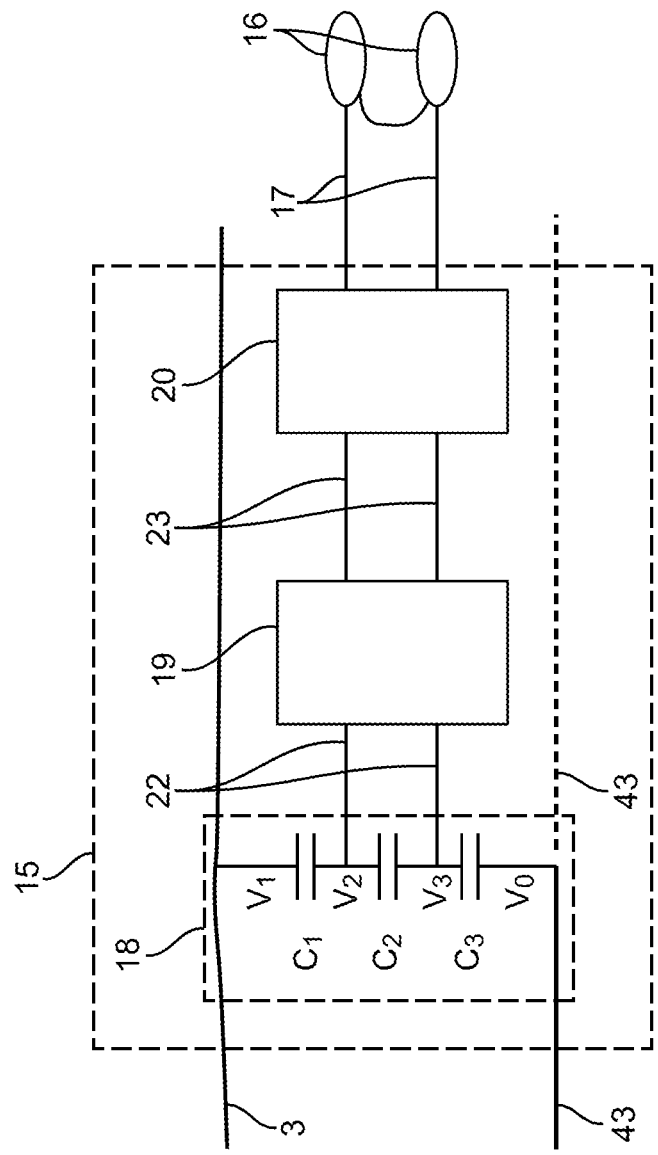
FIG. 11 illustrates an exemplary power conversion means using a voltage divider for voltage reduction means.

Using analytical methods well known to those skilled in the art a first order approximation of the voltage out of a capacitive voltage divider of the type illustrated in FIG. 11 can be made. If the following variables are defined:

$$V_{in}=V_1-V_0$$

$$V_{out}=V_2-V_3$$

$Z_x$=impedance for component x
and let $C_1=C_3=C$ so that the impedance $Z_i=Z_3=Z$ leads to $$V_{out}=V_{in}/(2*Z/Z_2+1).$$

Further recognizing that the impedance of an ideal capacitor (a reasonable approximation for example, ceramic capacitors at the frequencies encountered with electrosurgical generators) is $Z=1/(j*2*\pi*f)$ where j is the imaginary constant for the square root of −1 and f is frequency in Hz leads $V_{out}=V_{in}/(2*C_2/C+1)$ in which frequency is no longer a factor. This approximation ignores that $C_2$ has the parallel current path through the conductors between voltage reduction means 18 and rectification means 19 that also includes control and regulation means 20 through the conductors between rectification means 19 and control and regulation means 20. That parallel current path causes $V_{out}$ to have at least some sensitivity to frequency. With that added complexity $V_{out}$ is best determined based on the specific designs of rectification means 19 and control and regulation means 20 using specialized analytic tools such as circuit simulators known in the art such as SPICE (e.g. LTSPICE IV available from Linear Technology Corporation).

FIG. 12 shows an exemplary rectification means 19 in the form of a full-wave bridge rectifier. Rectification elements $D_1$, $D_2$, $D_3$, and $D_4$ are shown as diodes and may be any diode with a reverse recovery time compatible with the frequency of the output power of electrosurgical generators for which the circuit is to be used. Schottky diodes are particularly suitable as rectification elements $D_1$, $D_2$, $D_3$, and $D_4$ because they have almost no reverse recovery time. In general diodes or other rectification elements should switch with reverse recovery times preferably of less than about 400 nanoseconds with reverse recovery times preferably of less than about 100 nanoseconds being better and reverse recovery times preferably of less than about 50 nanoseconds being better. An example rectification element for $D_1$, $D_2$, $D_3$, and $D_4$ is MUR120 ultrafast diodes rated at 200V and with a reverse recovery time of 25 nanoseconds available from Vishay General Semiconductor.

The configuration shown in FIG. 12 with voltage reduction means 18 preceding rectification means 19 allows rectification elements for $D_1$, $D_2$, $D_3$, and $D_4$ to be rated for lower voltages than the voltage difference $V_{out}$, which, as mentioned earlier can have peak voltages of 5,000 volts or higher. FIG. 12 illustrates using filter capacitor $C_4$ following the bridge rectifier made from $D_1$, $D_2$, $D_3$, and $D_4$. Using filter capacitors is known to those skilled in the art and may be selected using methods known to those skilled in the art.

Control and regulation means 20 may be any means that adjusts and controls the power to one or more illumination elements 16 to have them perform within predetermined operating ranges, such as a predetermined current range. For example, control and regulation means 20 may control the current to one or more illumination elements to be within preferably about 10 to 1000 milliamps or to more preferably about between 10 to 500 milliamps or to more preferably between about 10 and 100 milliamps or more preferably between about 15 and 30 milliamps. Control and regulation means 20 may also adjust the voltage in some part of its circuit such as by using pulse width modulation. Voltage control and current control may both be used.

Figure 13:
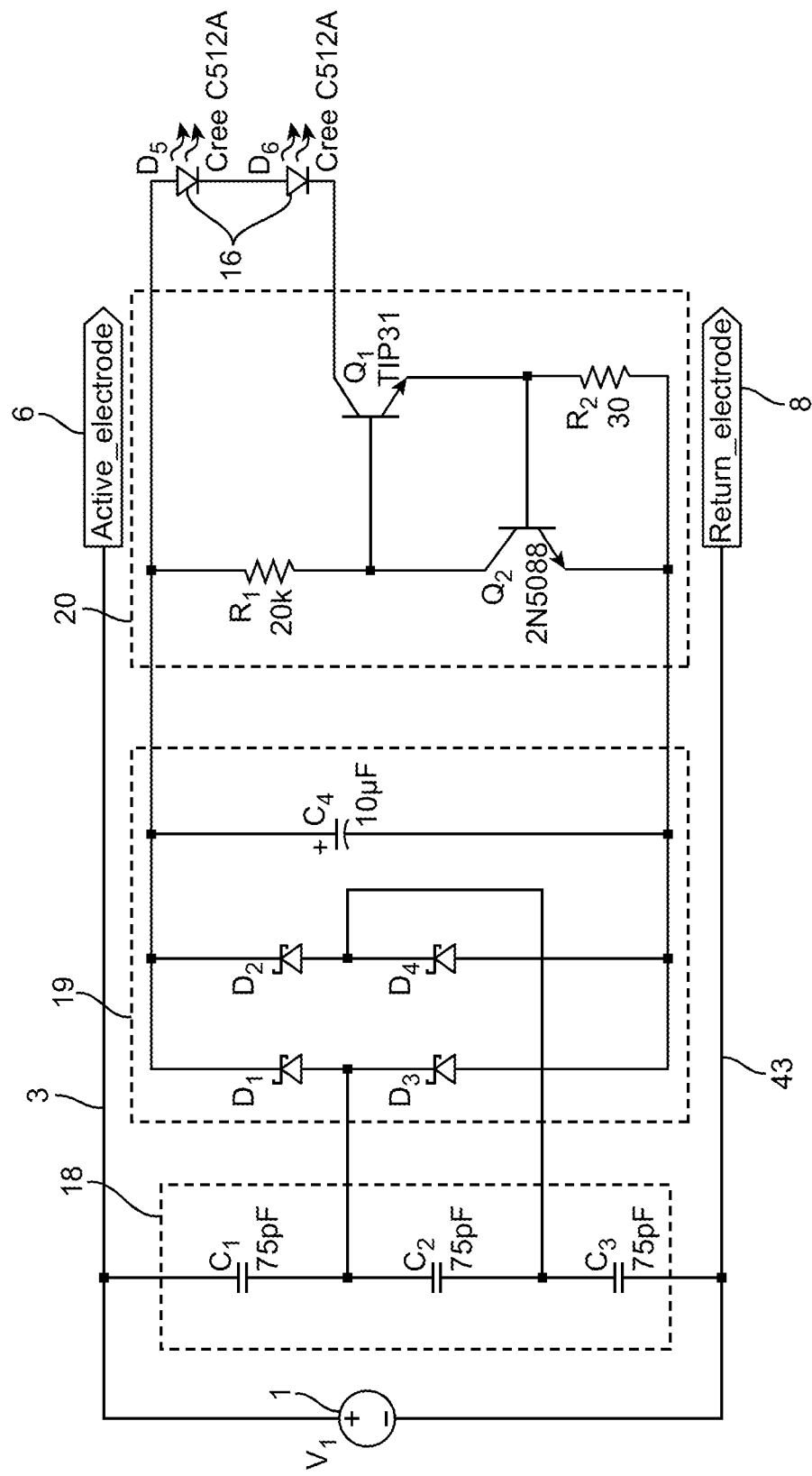
FIG. 13 is a schematic of an exemplary power conversion means.

FIG. 13 is an exemplary schematic showing exemplary circuits for voltage reduction means 18, rectification means 19, and control or regulation means 20. Here, exemplary rectification means 19 are Schottky diodes. Exemplary control and regulation means 20 uses two bipolar junction transistors, $Q_1$ and $Q_2$ to control the current to preferably about 20 milliamps through two illumination elements 16 using current sense resistor $R_2$. As will be appreciated by those skilled in the art other circuits for voltage reduction, rectification, and control or regulation are possible using electronic components that may include one or more active components possibly including bipolar junction transistors, field effect transistors, diodes, Schottky diodes, zener diodes, unijunction transistors, programmable unijunction transistors, operational amplifiers, comparators, voltage regulators, and possibly including one or more passive components including batteries, inductors, capacitors, resistors, and logic chips or transformers.

Figure 14:
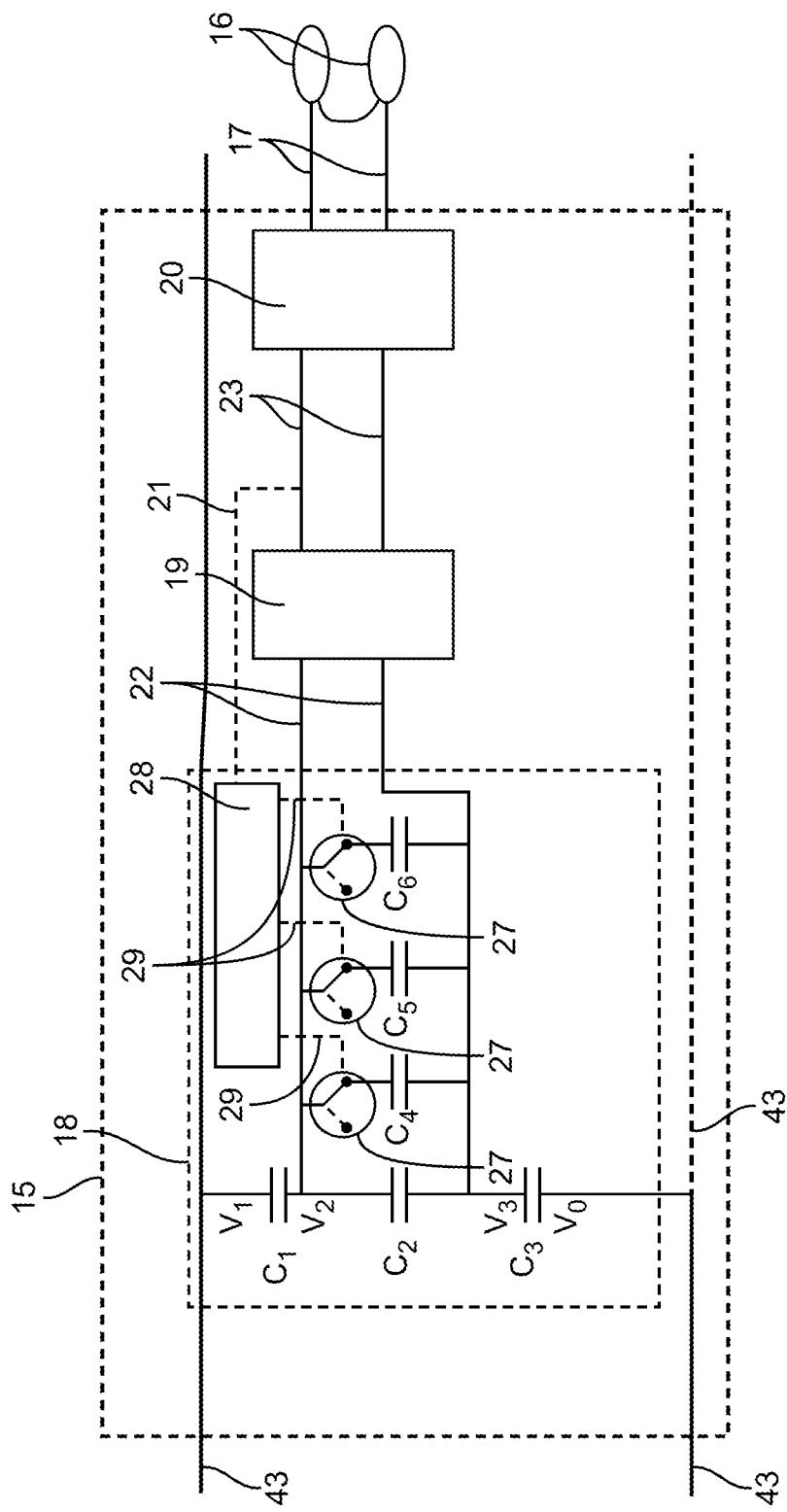
FIG. 14 illustrates exemplary power conversion means with a voltage divider responsive to rectification means output.

Voltage reduction means 18 may be responsive to an electrical parameter measured in power conversion means 15. FIG. 14 illustrates an exemplary configuration of a system that responds to voltage conveyed via electrical characteristics feedback conductor 21. Capacitors $C_2$, $C_4$, $C_5$, and $C_6$ are in parallel. Voltage reduction control switches 27 are controlled by switch control circuit 28 through switch control conductors 29. As is known to those skilled in the art, when capacitors are connected in parallel the total capacitance increases. Therefore, closing, for example the voltage reduction control switch 27 that switches $C_4$ will connect $C_2$ and $C_4$ in parallel leading to an increase in the capacitance in the middle of the voltage divider that also include $C_1$ and $C_3$. From before, the output voltage of the voltage divider with only $C_2$ is approximately $V_{out}=V_{in}/(2*C_2/C+1)$ and switching in $C_4$ effectively increases $C_2$ in this expression. The result is that as more capacitors are connected in parallel the output voltage from the voltage divider decreases for fixed input voltage. One example is to have in parallel with $C_2$ one or more capacitors with their associated switches (FIG. 14 has three capacitors $C_4$, $C_5$, and $C_6$ and switches 27 in parallel with $C_2$) and to start with switch control circuit 28 having all of the switches 27 closed so that the output voltage starts at a minimum value to ensure that the voltage ratings of components in rectification means 19 are not exceeded and to have switch control circuit 28 respond to the voltage signal carried via electrical characteristics feedback conductor 21 be used to selectively open one or more switches 27 to obtain an output voltage in a predetermined range.

FIG. 14 shows a responsive adjustable voltage divider in which capacitor elements are in parallel. The alternative configuration in which capacitors are switched in series as well as composite configurations with components switched in combinations of parallel and series may also be used.

Voltage reduction adjustment switches 27 may be mechanical switches such as relays or they may be comprised of one or more solid state devices including, but not limited to, diacs, triacs, and transistors, such as field effect transistors FETs, including pairs of FETs configured to collectively operate as a switch to conduct or block radiofrequency alternating current.

Switch control circuit 28 may have hysteresis (also referred to as "debounce") built into its switch controls so that one or more switches 27 stay open or closed with a tolerance band to prevent rapid on-off-on or off-on-off switching at the boundaries of one or more switching conditions. Control circuit elements that may be used include, but are not limited to, one or more batteries, operational amplifiers, comparators, unijunction transistors, programmable unijunction transistors, transistors, voltage regulators, diodes, zener diodes, capacitors, resistors, and logic chips. Batteries and zener diodes may be used to produce reference voltages. One or more embedded microcontrollers may also be used to control any aspect of the system including illumination, electrosurgery current or waveform, power, etc. The one or more embedded microcontrollers may be disposed anywhere in the system including in the handle, in a pendant coupled with any of the cables, in a connector that couples to any of the pins, etc.

Figure 15:
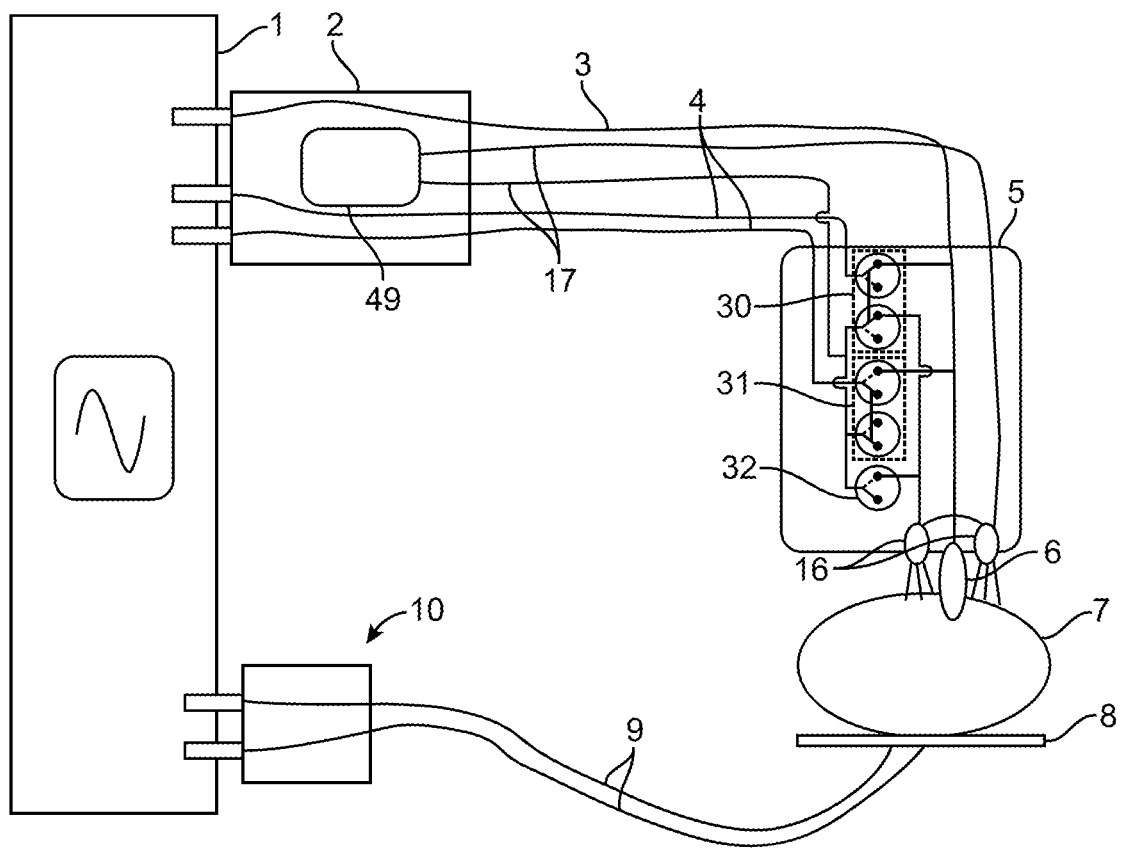
FIG. 15 illustrates exemplary illuminated electrosurgery with the power source in a plug and without using power from an electrosurgical generator.

FIG. 15 illustrates an exemplary configuration in which handle 5 has switches that enable power means 49 located in monopolar power connector plug 2 to power one or more illumination means 16 when either switch 30, switch 31, or switch 32 are activated. Switches 30 and 31 are double pole single throw switches that also activate each of the signal control lines 4 that allow electrosurgical generator 1 to deliver either cut or coagulation power. The configuration in FIG. 15 has three switches, 30 and 31 are double pole single throw and 32 is single pole single throw. Using switches 30 and 31 the user controls whether cut or coagulation power is delivered to tissue using one pole of the double pole single throw switch and in both cases the other pole controls illumination power to one or more illumination means 16 by power means 49. Therefore, activating switches 30 and 31 causes RF power to be delivered to tissue from generator 1 while illumination power comes from power means 49. Using switch 32 one or more illumination means 16 will be powered by power means 49 and neither cut nor coagulation power is delivered to tissue. Power means 49 could be a battery, fuel cell, or other energy source. Power means 49 could also be a capacitor charged by generator 1, such as by using a power conversion means described earlier. In that case connections (not shown in FIG. 15) to the active and return lines such as shown in FIG. 3 may be used to supply power to power conversion means 15 which may include a capacitor as power means 49.

Figure 16:
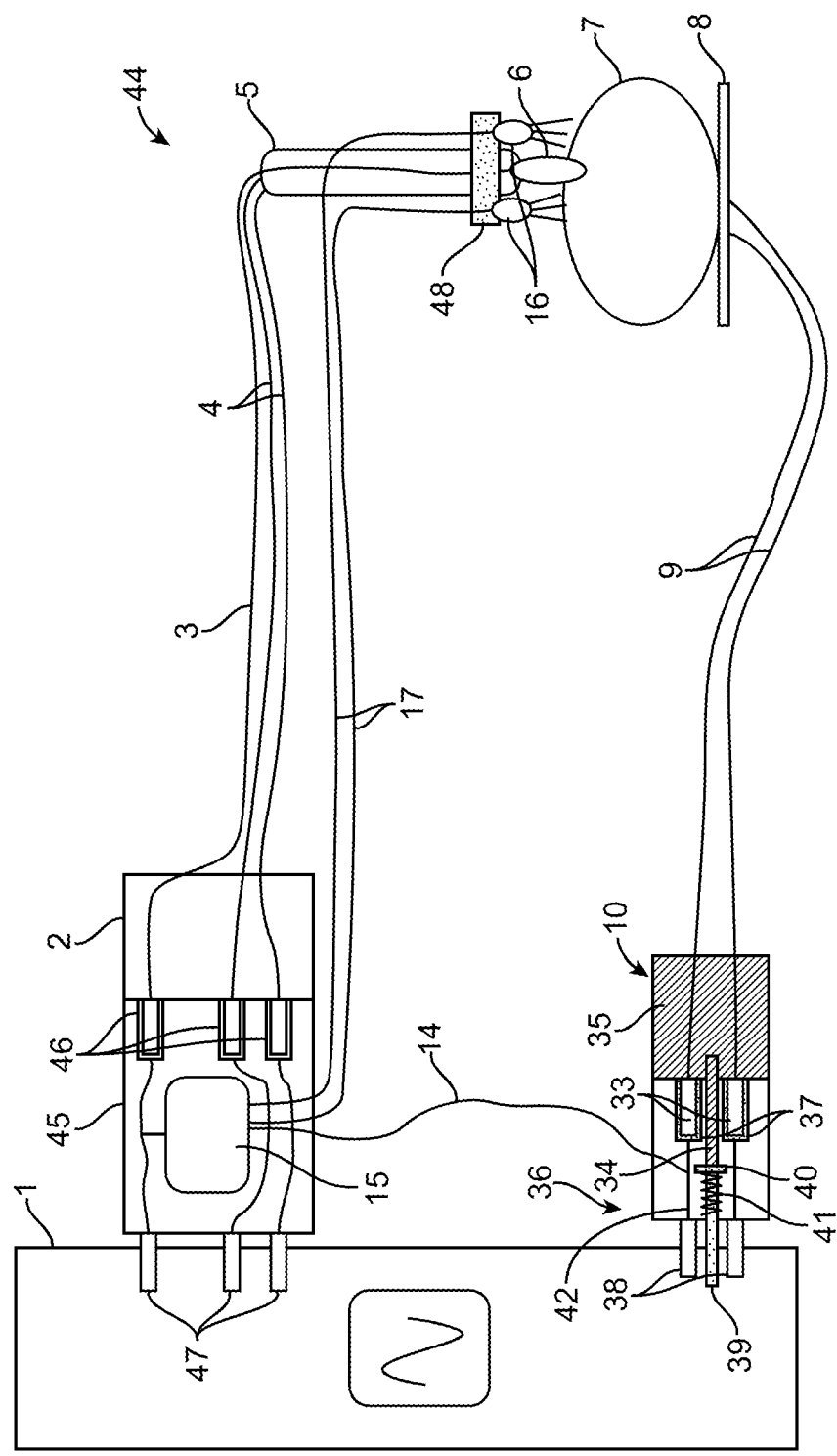
FIG. 16 illustrates exemplary illuminated electrosurgery with a conventional monopolar accessory connected to a power source adapter.

Another embodiment adapts conventional electrosurgical accessories to provide illumination from radiofrequency power extracted from electrosurgical generator power supplied to electrosurgical accessories or from alternative power means. FIG. 16 illustrates an exemplary configuration that adapts a conventional electrosurgical accessory 44 with an embodiment of the illumination technology. Monopolar power connector plug 2 (part of accessory 44) connects to power adapter module 45 by plugging into electrically conductive adapter connector jacks 46 that are electrically connected to adapter connector pins 47 that plug into the monopolar connector (not shown) of electrosurgical generator 1. Power adapter module 45 contains power conversion means 15. Alternatively, power conversion means 15 could be alternate power means 24 (not shown) described above. Power adapter means 45 has illumination power conductors 17 running from it to mounting means 48 that attaches to electrosurgical accessory handpiece 5 using clips (not shown), clamps (not shown), springs (not shown) or other suitable mechanical, adhesive, magnetic, or other means. Mounting means 48 holds illumination means 16 to handpiece 5 and routes wires and manages wires, cords, or cables associated with illumination power conductors 17. Illumination power conductors 17 may be wires in a cable or cord and may have clips (not show), bands (not shown), or other means that periodically affix or connect or attach illumination power conductors 17 to a wire or cable that has radiofrequency power conductor 3 and signal control lines 4 that are part of conventional electrosurgical accessory 44. The illumination element may be activated with buttons or switches on the electrosurgical instrument, or with a foot pedal.

FIG. 16 illustrates an embodiment that adapts a conventional monopolar accessory and with modifications that have both the active and return lines going to the adapter can be used with bipolar accessories.

Figure 17:
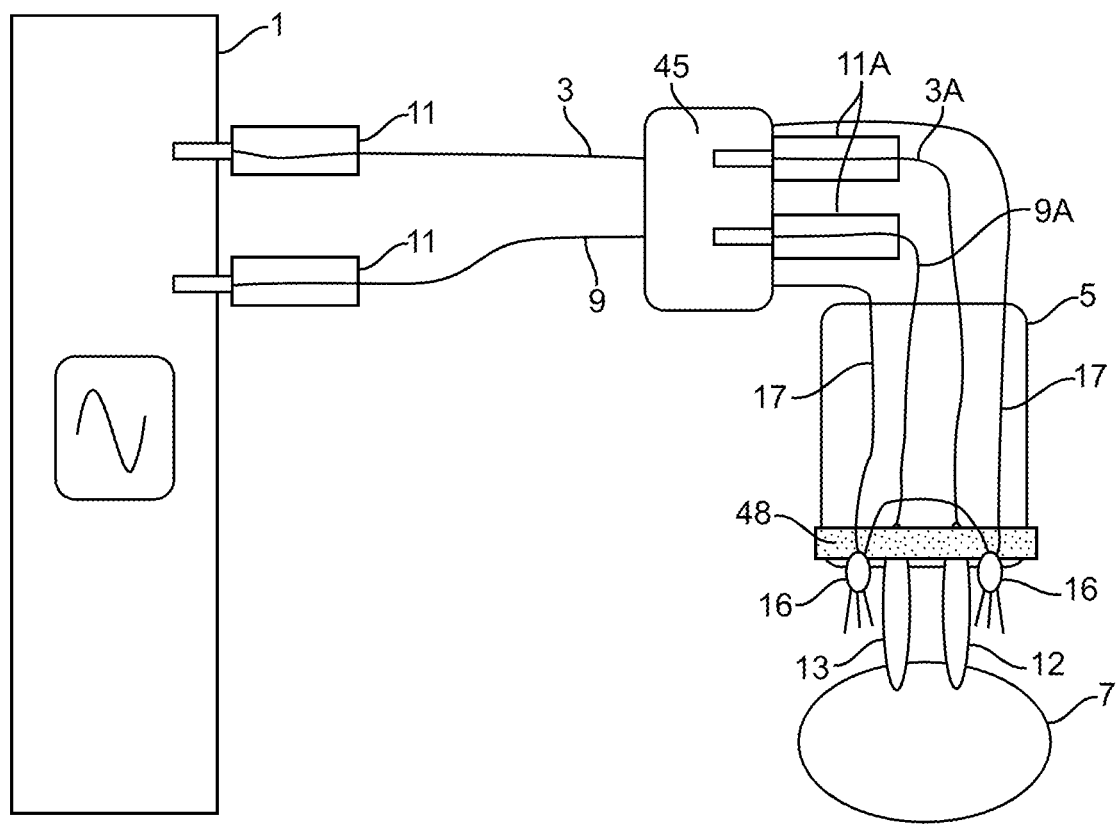
FIG. 17 illustrates exemplary illuminated electrosurgery with a conventional bipolar accessory connected to a power source adapter.

FIG. 17 illustrates a bipolar embodiment. Bipolar accessory has handpiece 5, connectors 11A, and active and return power conductors 3A and 9A. Power adapter means 45 is configured as a pendant as shown in FIG. 17 when generator 1 is a general purpose electrosurgical generator so that connectors 11 mate with those products. Power conversion means may be in a module that plugs directly into generator 1 if that generator is a special purpose product. Power adapter means 45 has illumination power conductors 17 running from it to mounting means 48 that attaches to electrosurgical accessory handpiece 5 using clips (not shown), clamps (not shown), springs (not shown) or other suitable mechanical, adhesive, magnetic, or other means.

Alternative Options.

The features describe above may be easily adapted to cooperate with existing electrosurgical instruments. If an illumination element is not already provided on the electrosurgical instrument, an LED or other illumination element may be coupled to the instrument such as in FIG. 16. Adapter plugs similar to what is described above may be used for monopolar systems. The monopolar adapter plug may be coupled to the electrosurgical power supply and an existing electrosurgical instrument may be plugged into the monopolar adapter. The monopolar adapter may have three pass through conductors 46, 47 from the electrosurgical instrument's plug to the electrosurgical power supply. The adapter 45 may have suitable electronics to power the illumination element and it may have two wires 17 to any light harness or clip 48 that is coupled to the existing electrosurgical instrument 5. These two wires 17 may be in a single cord or otherwise coupled to the instrument to manage cables and reduce clutter Similarly, the features described herein may also be used with other electrosurgical instruments such as bipolar forceps as seen in FIGS. 7 and 8. Bipolar forceps typically are powered whenever the surgeon depresses a footswitch (not illustrated) and usually after the forceps have grasped tissue (not illustrated). This power from generator 1 may also provide power to one or more illumination elements 16 and illuminate the surgical field when current is being delivered to tissue through electrodes 12 and 13. There may be instances when a surgeon prefers to illuminate the surgical field without delivering current to the tissue. Thus, an alternative power source such as a battery or capacitor may be used to power an illumination element when the radiofrequency generator is not activated. In that case a separate switch will be available to the surgeon such as on the bipolar handpiece. The battery or capacitor may optionally be charged when the generator 1 is providing power. The alternative power source may be disposed in a pendant as in FIG. 8 or in the instrument such as in FIG. 7, or a plug in module.

Figure 20A:
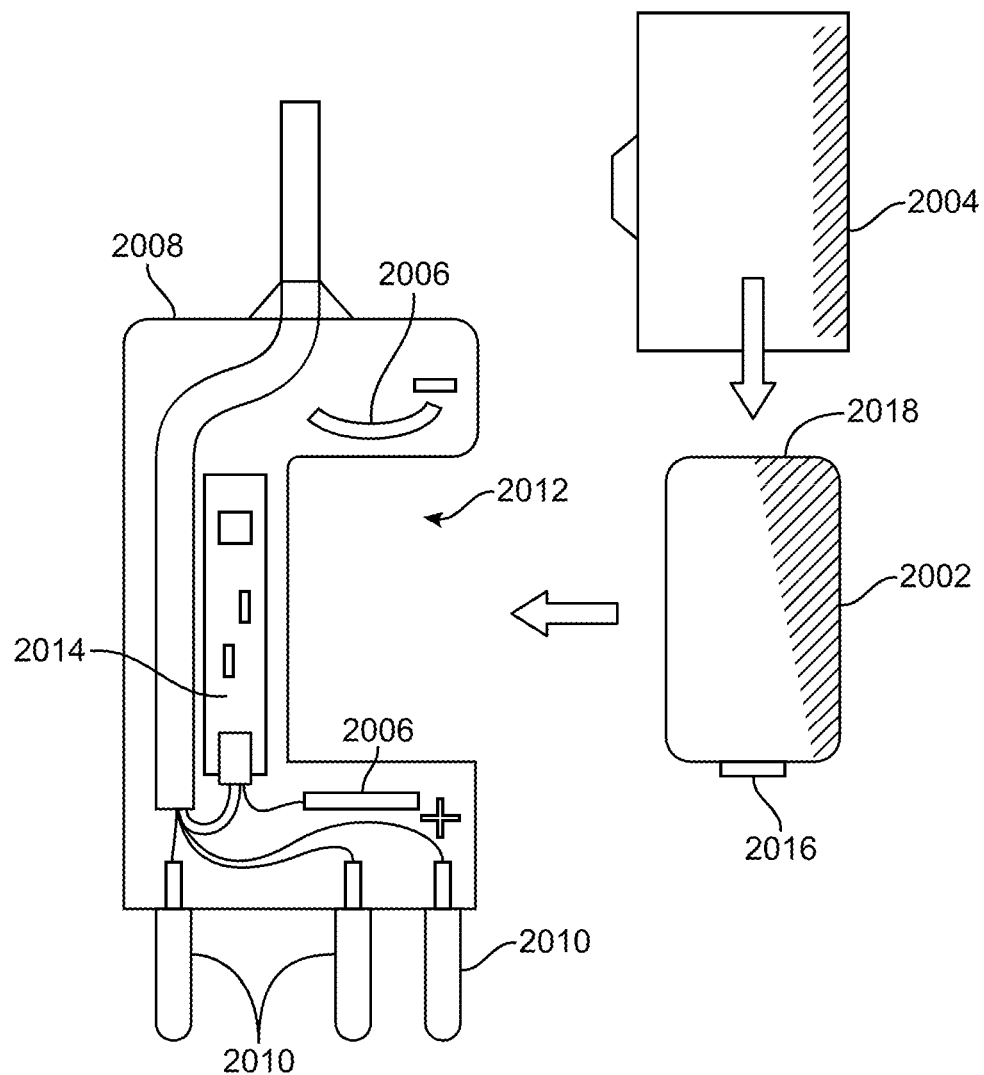
FIGS. 20A-20B illustrate a receptacle in a connector.
Figure 20B:
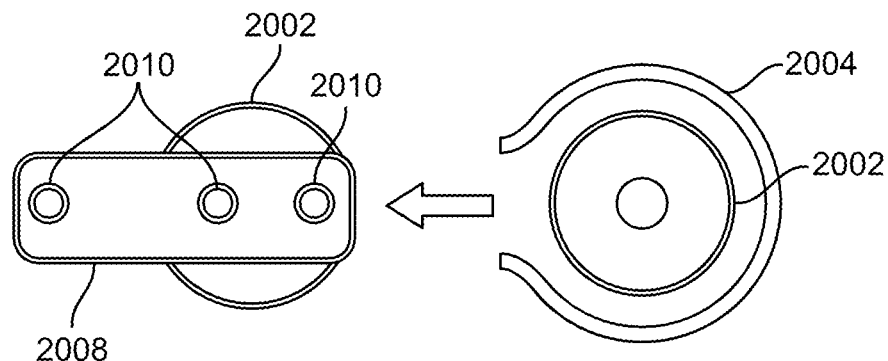

For example, FIGS. 20A-20B illustrate an optional battery compartment 202 that may be disposed in any of the connectors or plugs 2008 described herein. The connector 2008 inlcudes a recessed region 2012 which may be any shape such as square, rectangular, cylindrical, etc. and that is sized and shaped to receive a battery 2002 or capacitor or other energy storage unit of corresponding shape. The connector includes contacts 2006 that are also configured to electrically engage with the contacts 2016, 2018 on the batter or energy storage unit. Connector pins 2010 and a LED driver board 2014 are also visible. The battery 2002 is optionally disposed in a sleeve or cuff 2004, and the assembly is releasably attachable to and releasable from connector 2008. Therefore, if power runs out for the illumination element, the battery may be easily replaced outside of the sterile field without interrupting the surgical procedure since power may still be supplied by the RF generator to the electrode to cut or coagulate tissue during surgery. FIG. 20B shows an end view of the battery disposed in the battery compartment of the plug or connector.

Additionally, some embodiments may include other elements requiring power to operate, such as a camera, sensor, ultrasound transducer, etc. These additional powered elements may be used in conjunction with any of the illumination elements described here, and they may be powered using any of the techniques described herein. Or, in alternative embodiments, the illumination element may be substituted with a different powered element and powered using the techniques described herein.

Recent illuminated suction instruments with or without electrodes may also use the some or all of the features described herein. The illuminated suction instrument may comprise a suction tube that is coupled to a vacuum source, and an illumination element such as an LED, fiber optic or waveguide coupled to a light source may be coupled to the suction tube. The suction tube may have electrodes disposed on the suction tube for delivering current to the patient. Thus, the illumination element may receive power from a power source such as a radiofrequency generator while the electrodes on the suction tube are delivering current to tissue, or when illumination only is desired without current delivery to tissue. The electrodes may be separate electrodes coupled to the suction tube, or the suction tube may have masked areas which forms unmasked conductive regions which can serve as electrodes.

Some embodiments may include three switches such as in FIG. 6. One to active CUT mode, one to activate COAG mode, and a third to activate only illumination without current delivery to tissue.

Figure 18:
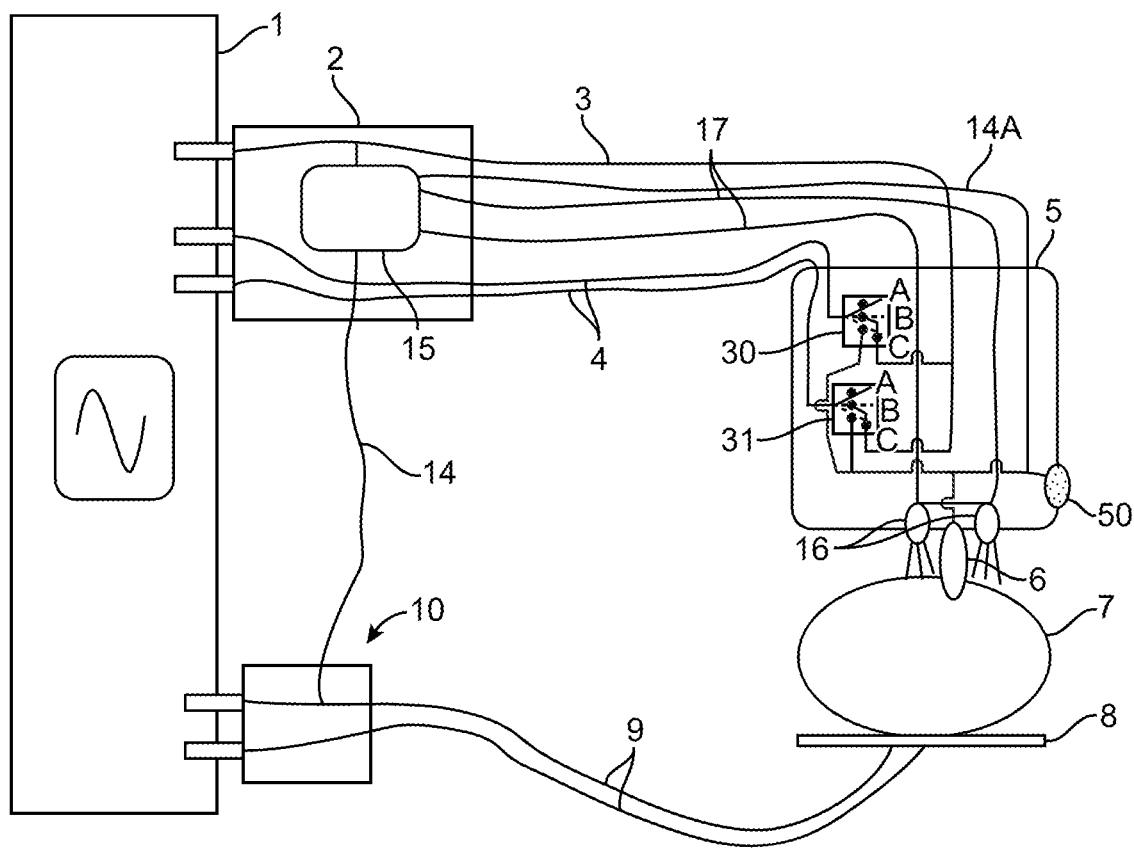
FIG. 18 illustrates exemplary illuminated electrosurgery with a monopolar accessory using switches with three positions to control illumination and power mode.

An alternative embodiment may have two switches controlling whether CUT or COAG power is applied to tissue with each switch having more than two positions such as in FIG. 18. Activating switches 30 and 31 each have three positions, A, B, and C. One of switches 30, 31 controls whether generator 1 operates in CUT mode and the other switch controls whether generator 1 operates in COAG mode. For both switches 30, 31, in position A the signals from control lines 4 are not connected to active electrode line 3 and generator 1 is not active and no RF power is produced and both illumination means 16 are not powered nor is power delivered to patient 7. When either switch 30 and 31 is in position B the signal from a control line 4 connects to active electrode line 3 and generator 1 is active and delivers RF power. In position B the active electrode 6 is not connected through the switches 30 or 31 to active electrode power so no power is supplied to patient 7. In position B power goes to illumination means 16. In position C the signal from a control line 4 connects to active electrode line 3 and generator 1 is active and delivers RF power, the same as occurs in position B. However, in position C the active electrode 6 is connected through the switches 30 or 31 to active electrode power and power is supplied to patient 7. Therefore, position A has both illumination off and patient power off, position B has only illumination on, and position C has both illumination and power to patient on.

FIG. 18 shows optional pilot light 50 that illuminates when power to the patient is active. Pilot light 50 illuminates when power to active electrode 6 is on, whether or not active electrode 6 is contacting patient 7. Pilot light 50 receives power from the line that powers active electrode 6 and the circuit for pilot light 50 completes in the example shown in FIG. 18 through return power line 14A. Return power line 14A is electrically connected to return line 14 although a current control element such as a resistor or other electronic components such as bipolar transistors, field effect transistors, comparators, voltage regulators, or operational amplifiers may be used. An example configuration is to put a 1 Mohm resistor in series with return power line 14A and to use a 2ML neon lamp available from Chicago Miniature Lamp, Inc. for pilot light 50. This example configuration will have pilot lamp 50 glow brightly when the power setting of generator 1 is greater than about 15 to 25 watts.

Indicator light or pilot light 50 may be any light source such as gas discharge lamps such as neon lamps, or LEDs or incandescent lamps. Gas discharge lamps such as neon lamps are particularly beneficial because they have high voltage capability that facilitates incorporating them with the high voltages employed with electrosurgery. Gas discharge lamps such as neon lamps also tolerate wide voltage ranges which facilitates incorporating them with the voltage ranges employed with electrosurgery. Gas discharge lamps also operate at low temperatures compared to, for example, incandescent lamps. Other configurations may have multiple colors such as using LEDs with different colors. For example, one color may indicate illumination only with no current being delivered to the tissue. Another color may indicate that illumination and cutting power are provided, or illumination and coagulation power are provided. Indicator lights may also be used as a part of a display such as an alpha numeric display, LCD, LED, or OLED display.

Figure 19:
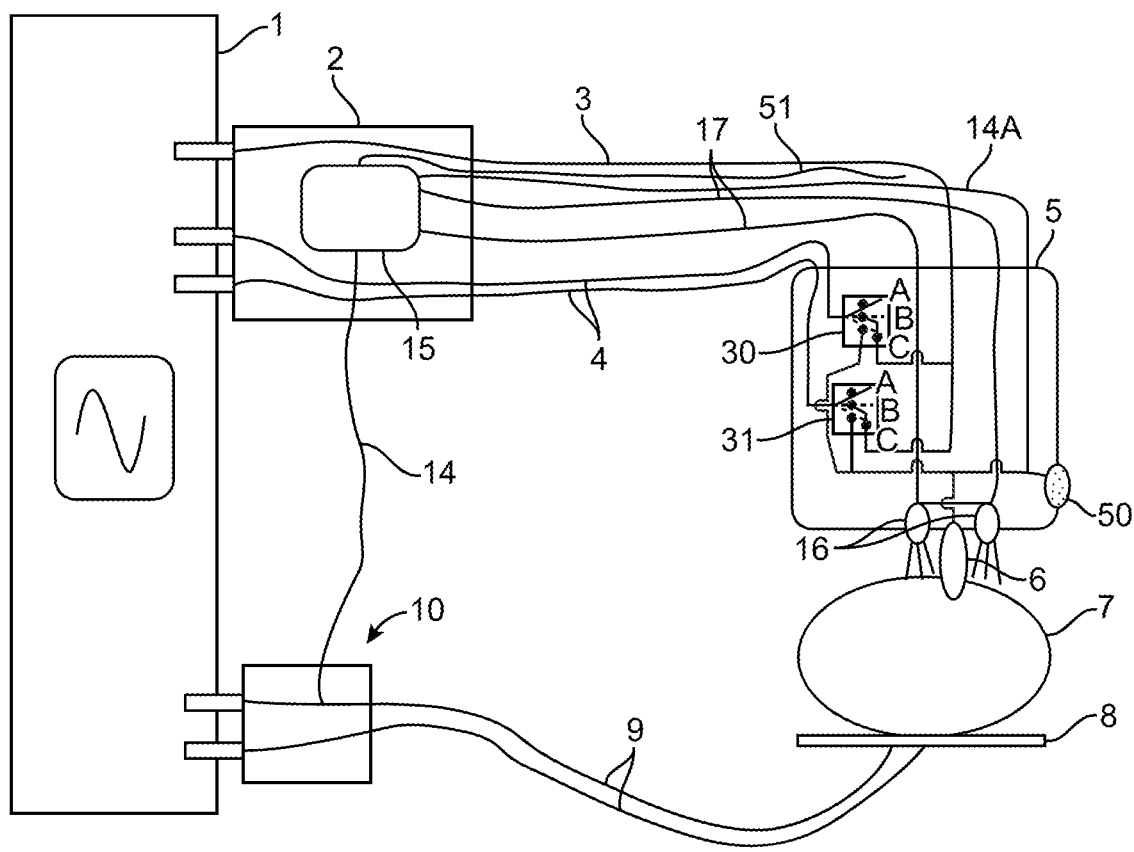
FIG. 19 illustrates an exemplary embodiment of illuminated electrosurgery where radiated energy is used to power the illumination means.

FIG. 19 illustrates an embodiment that does not extract power from the active electrode power of generator 1. Illumination power in the FIG. 19 embodiment comes from open conductor 51 that may be incorporated into the same cable or cord as active electrode line 3 or it may be separate. Power conversion means 15 may be omitted or it may be any of the configurations disclosed herein. Illumination means may preferably be one or more LEDs or gas discharge lamps such a neon lamps. An example LED that may be used is Cree C512A manufactured by Cree, Inc. of Durham, N.C. An example neon lamp that may be used is 2ML manufactured by Chicago Miniature Lamp. The length of open conductor 51 is preferably longer than about one foot and less than about 30 feet and more preferably longer than about three feet and less than about 18 feet. The configuration may include an open conductor 51 about four to ten feet long using the power conversion means 15 of FIG. 13 with open conductor 51 replacing active electrode conductor 3. Open conductor 51 does not need to be adjacent to conductors carrying RF power such as active electrode conductor 3. Without being limited to any particular theory or mode of operation it is believed that open conductor 51 harvests RF electromagnetic radiated power. A related configuration may be employed wherein open conductor 51 is configured adjacent to one or more conductors carrying RF power such that energy is extracted using at least some inductive coupling.

LEDs or other illumination means may or may not be mounted on a printed circuit board (PCB), or they can be coupled to a flexible printed circuit, and they can be effective sources of illumination. However, depending on how far the light source is from the distal tip, sufficient light may or may not be provided for illuminating the surgical field. In the case of removable surgical tips or electrosurgical tips which can be coupled to an electrosurgical handle, a long tip may cause a problem of insufficient light since the LED is on the handle, far away from the surgical field. A telescoping tube may be used to overcome this challenge. The tube telescopes in and out of an electrosurgical instrument. A ring LED may be coupled to the telescoping tube and the telescoping tube length may be adjusted to bring the LED to close to an optical tube so regardless of tip length, the light will always be in a desired position for delivering light. The LEDs are preferably mounted to the telescoping tube, and not to the housing of the electrosurgical instrument. One exemplary embodiment of this includes the illumination element coupled to a distal portion of the telescoping tube and thus the light is always close to the work area or surgical field. In another embodiment, the illumination element may be disposed on a proximal portion of the telescoping tube. Light is transmitted from the light source distally to the surgical field with fiber optic cables or a waveguide. The telescoping tube may be the waveguide and transmit the light. A third variation includes illumination elements near the middle of the telescoping tube and the light may be transmitted distally with a waveguide or fiber optics. The telescoping tube may also be a waveguide for transmitting the light. In still another embodiment, the illumination element is disposed on a distal portion of the electrosurgical instrument so it is always close to the surgical field.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for illuminating a surgical field, said system comprising:
    a connector plug configured to receive, from an electrosurgical generator, radiofrequency power at an output voltage;
    a power conductor extending from the connector plug to a proximal end of an electrosurgical instrument;
    an electrosurgical electrode at a distal end of the electrosurgical instrument, wherein the electrosurgical electrode is operably coupled to the electrosurgical generator by the power conductor and the connector plug, wherein the electrosurgical electrode is configured to use the radiofrequency power to perform electrosurgery on tissue;
    a power conversion module configured to extract a portion of the radiofrequency power and convert the portion of the radiofrequency power to a secondary power having a second voltage, wherein the second voltage is different than the output voltage;
    an illumination element electrically coupled with the power conversion module, wherein the illumination element is configured to use the secondary power to emit light for illuminating the surgical field; and
    at least one switch that is actuatable to provide the secondary power to the illumination element without simultaneously providing the radiofrequency power to the electrosurgical electrode.

2. The system of claim 1, wherein the at least one switch comprises:
    a first switch that is actuatable between: (i) a first position in which the secondary power is provided to the illumination element without providing the radiofrequency power to the electrosurgical electrode and (ii) a second position in which the secondary power is provided to the illumination element and the radiofrequency power is simultaneously provided to the electrosurgical electrode.

3. The system of claim 2, wherein the at least one switch further comprises:
    a second switch that is actuatable between: (i) a first position in which the secondary power is provided to the illumination element without providing the radiofrequency power to the electrosurgical electrode and (ii) a second position in which the secondary power is provided to the illumination element and the radiofrequency power is simultaneously provided to the electrosurgical electrode,
    wherein when the first switch is in the second position the radiofrequency power has a first waveform that is configured for cutting the tissue with the electrosurgical electrode,
    wherein when the second switch is in the second position the radiofrequency power has a second waveform that is configured for coagulating the tissue with the electrosurgical electrode, and
    wherein the first waveform is different than the second waveform.

4. The system of claim 1, wherein the at least one switch comprises:
    a first switch that is actuatable to provide the secondary power to the illumination element without providing the radiofrequency power to the electrosurgical electrode;
    a second switch that is actuatable to simultaneously provide (i) the secondary power to the illumination element and (ii) the radiofrequency power to the electrosurgical electrode with a first waveform configured for cutting the tissue; and
    a third switch that is actuatable to simultaneously provide (i) the secondary power to the illumination element and (ii) the radiofrequency power to the electrosurgical electrode with a second waveform configured for coagulating the tissue,
    wherein the first waveform is different than the second waveform.

5. The system of claim 1, wherein the power conversion module comprises a voltage reduction means.

6. The system of claim 1, wherein the power conversion module further comprises a rectifying means configured to receive the portion of the radiofrequency power and configured to output the secondary power as a direct current power.

7. The system of claim 6, wherein the rectifying means comprises one or more diodes and a transformer.

8. The system of claim 1, wherein the power conversion module is in the connector plug.

9. The system of claim 1, wherein the power conversion module is in a handle portion of the electrosurgical instrument.

10. The system of claim 1, wherein the illumination element is in a handle portion of the electrosurgical instrument.

11. The system of claim 10, further comprising a waveguide configured to receive the light emitted by the illumination element and transmit the light distally from the illumination element to the surgical field.

12. The system of claim 11, further comprising a telescoping tube configured to telescope in and out of the handle portion of the electrosurgical instrument, wherein the telescoping tube comprises the waveguide.

13. The system of claim 1, further comprising:
    a return electrode configured to receive the radiofrequency power from the tissue;
    a return power conductor configured to provide the radiofrequency power from the return electrode to the electrosurgical generator; and
    a supplemental return conductor that couples the power conversion module to the return power conductor.

14. A method for illuminating or facilitating treatment of a surgical field, said method comprising:
    providing an electrosurgery instrument comprising:
        a connector plug configured to receive, from an electrosurgical generator, radiofrequency power at an output voltage;
        a power conductor extending from the connector plug to a proximal end of an electrosurgical instrument;
        an electrosurgical electrode at a distal end of the electrosurgical instrument, wherein the electrosurgical electrode is operably coupled to the electrosurgical generator by the power conductor and the connector plug, wherein the electrosurgical electrode is configured to use the radiofrequency power to perform electrosurgery on tissue;
        a power conversion module configured to extract a portion of the radiofrequency power and convert the portion of the radiofrequency power to a secondary power having a second voltage, wherein the second voltage is different than the output voltage;
an illumination element electrically coupled with the power conversion module, wherein the illumination element is configured to use the secondary power to emit light for illuminating the surgical field; and
at least one switch that is actuatable to provide the secondary power to the illumination element without simultaneously providing the radiofrequency power to the electrosurgical electrode
actuating the at least one switch to provide the secondary power to the illumination element without simultaneously providing the radiofrequency power to the electrosurgical electrode; and
responsive to actuating the at least one switch, illuminating the surgical field with light from the illumination element.

15. The method of claim 14, wherein the at least one switch comprises a first switch, and
wherein actuating the at least one switch comprises:
actuating the first switch to a first position to provide the secondary power to the illumination element without simultaneously providing the radiofrequency power to the electrosurgical electrode, and
actuating the first switch to a second position to simultaneously provide the secondary power to the illumination element and the radiofrequency power to the electrosurgical electrode.

16. The method of claim 15, wherein the at least one switch further comprises a second switch,
wherein actuating the at least one switch comprises:
actuating the second switch to a first position to provide the secondary power to the illumination element without simultaneously providing the radiofrequency power to the electrosurgical electrode, and
actuating the second switch to a second position to simultaneously provide the secondary power to the illumination element and the radiofrequency power to the electrosurgical electrode,
wherein when the first switch is in the second position the radiofrequency power has a first waveform that is configured for cutting the tissue with the electrosurgical electrode,
wherein when the second switch is in the second position the radiofrequency power has a second waveform that is configured for coagulating the tissue with the electrosurgical electrode, and
wherein the first waveform is different than the second waveform.

17. The method of claim 14, wherein actuating the at least one switch comprises:
actuating a first switch to provide the secondary power to the illumination element without providing the radiofrequency power to the electrosurgical electrode,
actuating a second switch to simultaneously provide (i) the secondary power to the illumination element and (ii) the radiofrequency power to the electrosurgical electrode with a first waveform configured for cutting the tissue, and
actuating a third switch to simultaneously provide (i) the secondary power to the illumination element and (ii) the radiofrequency power to the electrosurgical electrode with a second waveform configured for coagulating the tissue,
wherein the first waveform is different than the second waveform.

18. The method of claim 14, wherein the power conversion module is in the connector plug.

19. The method of claim 14, wherein the power conversion module is in a handle portion of the electrosurgical instrument.

20. The method of claim 14, wherein the illumination element is in a handle portion of the electrosurgical instrument,
wherein the electrosurgical instrument comprises a telescoping tube configured to telescope in and out of the handle portion of the electrosurgical instrument, wherein the telescoping tube comprises a waveguide configured to receive the light emitted by the illumination element and transmit the light distally from the illumination element to the surgical field, and
wherein the method further comprises telescopically moving the telescoping tube relative to the handle portion.

* * * * *